(12) United States Patent
Hansen et al.

(10) Patent No.: US 8,696,764 B2
(45) Date of Patent: Apr. 15, 2014

(54) FURTHER IMPROVEMENTS TO ANKLE-FOOT PROSTHESIS AND ORTHOSIS CAPABLE OF AUTOMATIC ADAPTATION TO SLOPED WALKING SURFACES

(75) Inventors: Andrew H. Hansen, Apple Valley, MN (US); Eric A. Nickel, Brooklyn Park, MN (US)

(73) Assignee: Northwestern University, Evanston, IL (US)

(*) Notice: Subject to any disclaimer, the term of this patent is extended or adjusted under 35 U.S.C. 154(b) by 0 days.

(21) Appl. No.: 13/374,881

(22) Filed: Jan. 20, 2012

(65) Prior Publication Data

US 2013/0006386 A1 Jan. 3, 2013

Related U.S. Application Data

(60) Provisional application No. 61/461,703, filed on Jan. 20, 2011.

(51) Int. Cl.
*A61F 2/66* (2006.01)
*A61F 5/01* (2006.01)

(52) U.S. Cl.
USPC ............... 623/52; 623/53; 606/27; 606/16

(58) Field of Classification Search
USPC ............ 623/27, 47, 48, 49, 50, 52, 53; 602/5, 602/16, 23, 26, 27
See application file for complete search history.

(56) References Cited

U.S. PATENT DOCUMENTS

| | | | |
|---|---|---|---|
| 3,045,247 A * | 7/1962 | Bair | ............................... 623/49 |
| 4,360,931 A | 11/1982 | Hampton | |
| 4,413,360 A | 11/1983 | Lamb | |
| 4,547,913 A | 10/1985 | Phillips | |
| 4,555,817 A | 12/1985 | McKendrick | |
| 6,159,248 A | 12/2000 | Gramnas | |
| 6,217,249 B1 | 4/2001 | Merlo | |
| 6,436,149 B1 | 8/2002 | Rincoe | |
| 6,443,993 B1 | 9/2002 | Koniuk | |
| 6,500,138 B1 | 12/2002 | Irby | |
| 7,431,737 B2 | 10/2008 | Ragnarsdottir et al. | |
| 7,637,957 B2 | 12/2009 | Ragnarsdottir | |
| 7,637,959 B2 | 12/2009 | Clausen | |
| 7,811,334 B2 | 10/2010 | Ragnarsdottir et al. | |
| 7,896,927 B2 | 3/2011 | Clausen et al. | |
| 8,057,550 B2 | 11/2011 | Clausen | |

(Continued)

OTHER PUBLICATIONS

International Preliminary Report on Patentability for Int'l App. No. PCT/US2012/000038, dated Jul. 23, 2013.

(Continued)

*Primary Examiner* — Marcia Hoffman

(74) *Attorney, Agent, or Firm* — Cook Alex Ltd.

(57) ABSTRACT

The present invention relates to an improved system for use in rehabilitation and/or physical therapy for the treatment of injury or disease to the lower limbs or extremities. The system can enable an amputee to proceed over any inclined or declined surface without overbalancing. The system is mechanically passive in that it does not utilize motors, force generating devices, batteries, or powered sources that may add undesirable weight or mass and that may require recharging. In particular the system is self-adapting to adjust the torque moment depending upon the motion, the extent of inclination, and the surface topography. An additional advantage of the improvement is that the system can be light and may also be simple to manufacture.

6 Claims, 12 Drawing Sheets

(56) References Cited

U.S. PATENT DOCUMENTS

| | | |
|---|---|---|
| 2004/0064195 A1 | 4/2004 | Herr |
| 2004/0153168 A1 | 8/2004 | Childress et al. |
| 2005/0192677 A1 | 9/2005 | Ragnarsdottir |
| 2005/0197717 A1 | 9/2005 | Ragnarsdottir |
| 2006/0184280 A1 | 8/2006 | Oddsson |
| 2006/0224246 A1 | 10/2006 | Clausen et al. |
| 2006/0224247 A1 | 10/2006 | Clausen |
| 2006/0249315 A1 | 11/2006 | Herr |
| 2007/0043449 A1 | 2/2007 | Herr et al. |
| 2008/0215161 A1 | 9/2008 | Ragnarsdottir |
| 2009/0222105 A1 | 9/2009 | Clausen |
| 2010/0030344 A1 | 2/2010 | Hansen et al. |
| 2010/0185301 A1 | 7/2010 | Hansen |
| 2011/0106274 A1 | 5/2011 | Ragnarsdottir et al. |
| 2011/0224804 A1 | 9/2011 | Clausen |
| 2011/0245931 A1 | 10/2011 | Clausen |

OTHER PUBLICATIONS

Feldman, Once More on the Equilibrium-point Hypothesis (lambda model) for Motor Control, J. Motor Behav., 18, 1986, pp. 17-54.

Perry, Gait Analysis: Normal and Pathological Function, 1992, Slack Inc., 1992.

Latash et al., Joint Stiffness: Myth or Reality?; Hum. Mov. Sci, 12, 1993, pp. 653-692.

Irby et al., Optimization and Application of a Wrap-Spring Clutch to a Dynamic Knee-Ankle-Foot Orthosis, IEEE Trans. Rehabil. Eng., 7, 2, 1999, pp. 130-134.

Ferris et al., Runners Adjust Leg Stiffness for Their First Step on a New Running Surface; J. Biomech.; 32, 8, pp. 787-794, 1999.

Hansen, Roll-over Characteristics of Human Walking With Applications for Artificial Limbs; Dissertation, 2002.

Leroux et al., Postural Adaptations to Walking on Inclined Surfaces: I. Normal Strategies, Gait & Pos., 15, 1, 2002, pp. 67-74.

Hansen et al., The Human Ankle During Walking: Implications for Design of Biomimetic Ankle Prostheses, J. Biomech; 37, 10, pp. 1467-1474.

Hansen et al., Roll-over Characteristics of Human Walking on Inclined Surfaces; Hum. Mov, Sci.; 23, 6, pp. 807-821.

Prentice et al., Locomotor Adaptations for Changes in Slope of the Walking Surface; Gait & Pos.; 20, 3, pp. 255-265.

Lay, The Effects of Sloped Surfaces on Locomotion: A Kinematic and Kinetic Analysis, J. Biomech., 39, 9, 2006, pp. 1621-1628.

Williams et al., Prosthetic Ankle-Foot Mechanism Capable of Automatic Adaptation to the Walking Surface; J. Biomech. Eng., 131, 3, 2009.

Alimusaj at al., Kinematics anfd Kinetics with an Adaptive Ankle Foot System Duting Stair Ambulation of Transtibial Amputees; Gait & Pos.; 30, 3, 2009 pp. 356-363.

Wolf at al., Pressure Characteristics at the Stump/Socket Interface in Transibital Amputees Using Adaptive Prosthetic Foot; Clin. Biomecha.; 24, 10, 2009, pp. 860-865.

Kangude et al., Single Channel Hybrid EFS Gait System Using an Energy Storage Orthosis: Preliminary Design, Proc. IEEE Eng. Med. Bio. Soc., 2009, pp. 6798-6801.

Fradet at al., Biomechanical Analysis of Ramp Ambulation of Transibital Amputees with an Adaptive Ankle Foot System; Gait & Pos.; 32, 3, 2010, pp. 191-198.

PCT/US2007/022208 International Search Report.

PCT/US2007/022208 Written Opinion of the International Search Authority.

PCT/US2011/000675 International Search Report.

PCT/US2011/000675 Written Opinion of the International Search Authority.

PCT/US2012/000038 International Search Report.

* cited by examiner

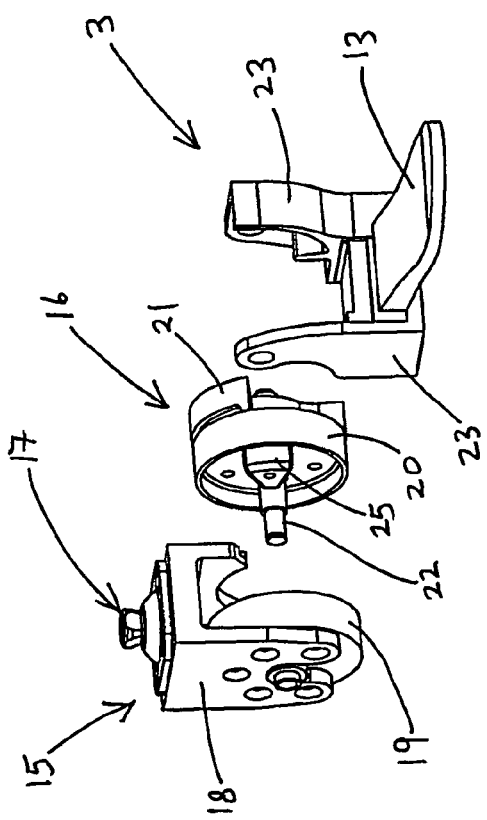
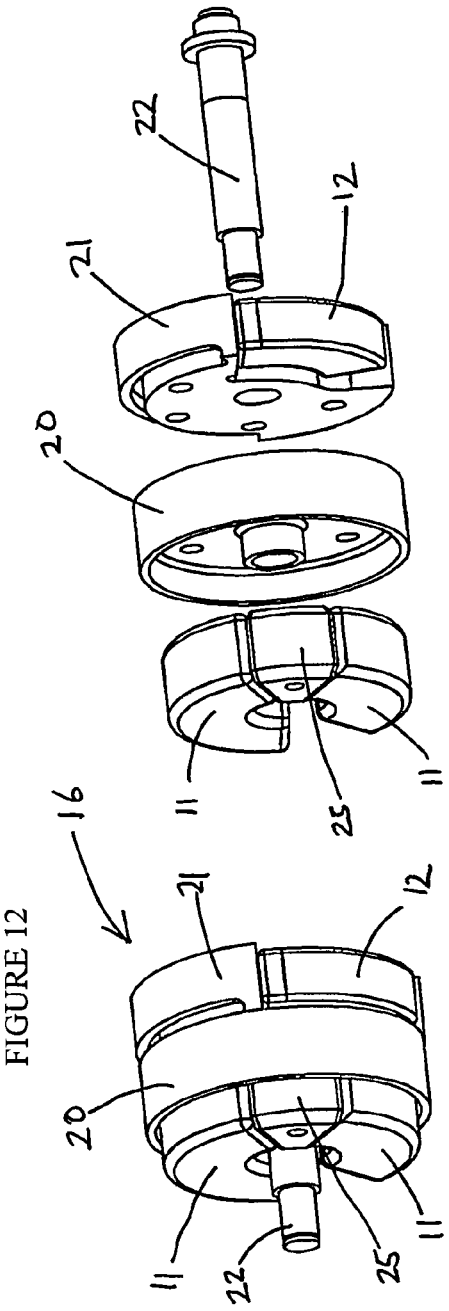
FIGURE 12
FIGURE 13

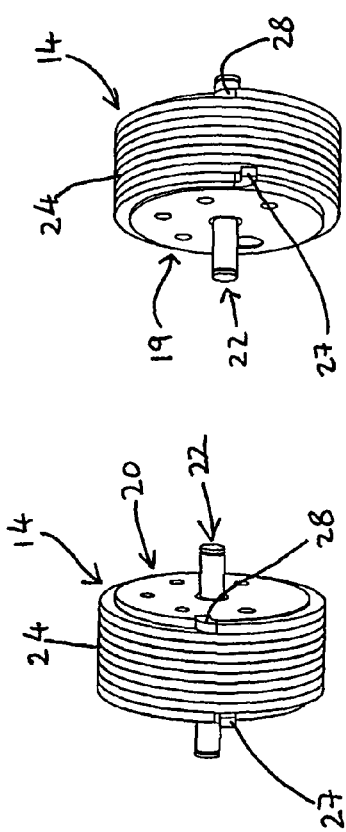
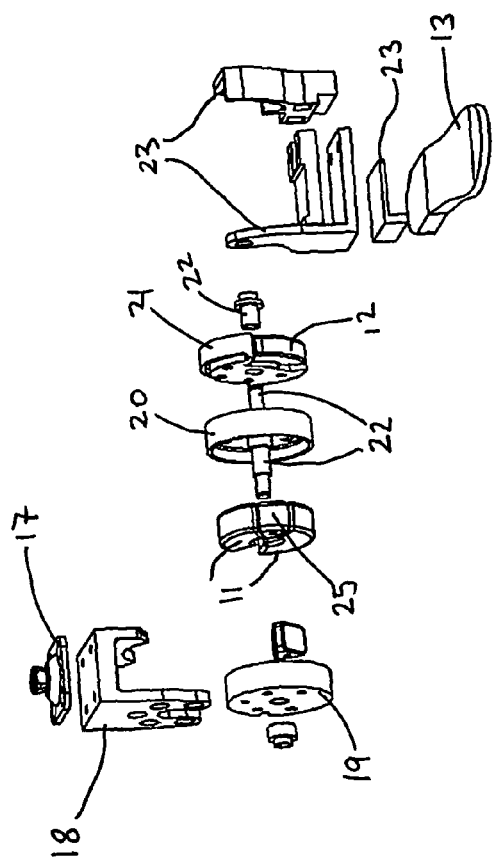

FURTHER IMPROVEMENTS TO ANKLE-FOOT PROSTHESIS AND ORTHOSIS CAPABLE OF AUTOMATIC ADAPTATION TO SLOPED WALKING SURFACES

The present application claims priority to U.S. Provisional Patent Application Ser. No. 61/461,703 entitled "Further Improvements to Passive Ankle-Foot Prosthesis Capable of Automatic Adaptation to Sloped Walking Surfaces and Methods of Use", filed 20 Jan. 2011, which is herein incorporated by reference in its entirety for all purposes.

This invention was made with government support under GM079300 awarded by National Institute of Health and H133E080009 awarded by the Department of Education (NIDDR). The government has certain rights in the invention.

TECHNICAL FIELD

The inventions relate to improved ankle-foot prosthetic and orthotic systems and methods of use. In particular the prosthetic or orthotic systems comprise an ankle unit that, in combination with other mechanical elements of prosthetic or orthotic systems, enable the gait of an individual using the device to emulate the gait of able-bodied individual and that automatically adapts the gait to different terrains and slopes on each and every step.

BACKGROUND ART

Many currently available prosthetic and orthotic ankle-foot mechanisms do not allow ankle motion. Rigid ankle prosthetic and orthotic ankle-foot devices generally attempt to replace the actions of the biologic ankle-foot system through deformations of their materials and/or by utilizing rocker shapes on the plantar surfaces. The prosthetic and orthotic ankle-foot devices that do incorporate ankle motion usually allow rotational motion about a single angle that does not change without mechanical adjustments of the prosthesis or orthosis. Some of these devices use springs and/or bumpers to store and release energy and return the device's ankle joint to one "equilibrium" point. This single and constant "equilibrium" point can result in good function on level terrain and when using shoes of one particular heel height (heel and forefoot sole differential). However, problems can arise when walking on different terrain or when using shoes of different heel height. The heel height problem can be fixed using a change in the alignment of the prosthesis. However, this is not a simple task and one that does not happen automatically.

A patent issued to Wayne Koniuk (U.S. Pat. No. 6,443,993 B1, "Self-Adjusting Prosthetic Ankle Apparatus", issued Sep. 3, 2002) discloses a device that will adapt to various terrains and to shoes of different heel height. However, Koniuk's design does not appear to have energy storage and release properties, utilizes more sensing devices than the proposed design, and does not appear to give plantarflexion at late stance. Koniuk's design is based on damping control of the ankle joint whereas the proposed device is based on the control of stiffness about the ankle. Damping removes energy from a system whereas stiffness can store and release energy to a system throughout a loading and unloading cycle (that is, a walking cycle).

Recent research has suggested that roll-over shape, the effective rocker shape that the ankle-foot system conforms to between heel contact and opposite heel contact, is an important characteristic for walking. Hansen ((2002); "Roll-over Characteristics of Human Walking With Applications for Artificial Limbs." Ph.D. dissertation, Northwestern University, Evanston, Ill.) found that the able-bodied ankle-foot system adapts to several walking conditions to maintain a similar roll-over shape and that its roll-over shape changes predictably when walking on inclined or declined surfaces. Specifically, able-bodied ankle-foot systems are capable of automatically adapting to differences in shoe heel height and to different surface inclinations. Current prosthetic ankle-foot mechanisms cannot automatically adapt to these conditions. Recently, prosthetic devices have come onto the market that claim adaptability to sloped surfaces, yet these devices have their limitations. For example, the Echelon (Endolite North America, Miamisburg, Ohio, USA), which has a series combination of spring and damper, is claimed to be able to self-align for varied terrain (as stated in product literature). This combination permits the foot plate to rotate through a nine degree arc (six degrees in plantarflexion and three degrees in dorsiflexion) before reaching the physical limits of the viscoelastic range of motion, at which point it transitions to a predominantly elastic range of motion produced by deflection of the foot plate.

On inclined and declined surfaces, the effective ankle angle at which the viscoelastic range transitions to the elastic range remains unchanged. Thus the Echelon does not mimic the change in equilibrium point of the anatomical ankle. Instead, it tolerates or accommodates changes in surface orientation.

The Motionfoot (Motion Control Inc., Salt Lake City, Utah, USA) also utilizes a series combination of spring and damper. While the Motionfoot has a greater range of viscoelastic motion than the Echelon, it also provides a single equilibrium point on sloped surfaces (that is, a single ankle angle for the end range of the damper, or dorsiflexion stop). In addition, the potential loss of energy from the damping of both the Echelon and Motionfoot may limit the ability of these prostheses to store and return energy to the user.

The Proprio Foot (Össur, Foothill Ranch, Calif., USA) actively adapts to surface orientation. It senses changes in surface orientation then actuates appropriate changes to effective prosthesis alignment. One of the limitations of the Proprio Foot is the timing of the adaptation. Adaptation occurs following the step where the sloped surface was detected, during swing phase. In addition, the change is incremental, thus a significant change in slope could require several steps before full adaptation is achieved. Another limitation of the Proprio Foot is its high cost.

In the real world, surfaces can change slope rapidly. Able-bodied persons are able to adjust their limb properties prior to encountering a new surface (see Ferris, D., Liang, K., and Farley, C., 1999, "Runners Adjust Leg Stiffness for Their First Step on a New Running Surface," J. Biomech., 32(8), pp. 787-794; Prentice, S., Hasler, E., Groves, J., and Frank, J., 2004, "Locomotor Adaptations for Changes in the Slope of the Walking Surface," Gait & Pos., 20(3), pp. 255-265). Yet uneven surfaces with rapidly changing slope could result in a Proprio Foot adapted for a decline when the user steps onto an incline or vice versa. Recent studies involving the Proprio Foot on sloped surfaces have had to preset the device to a "fully adapted" state based on the onboard adaptation algorithms and the surface slopes used in the studies to avoid this problem (Alimusaj, M., Fradet, L., Braatz, F., Gemer, H., and Wolf, S., 2009, "Kinematics and Kinetics With an Adaptive Ankle Foot System During Stair Ambulation of Transtibial Amputees," Gait & Pos., 30(3), pp. 356-363; Fradet, L., Alimusaj, M., Braatz, F., and Wolf, S., 2010, "Biomechanical Analysis of Ramp Ambulation of Transtibial Amputees with an Adaptive Ankle Foot System," Gait & Pos., 32(2), pp. 191-198; and Wolf, S., Alimusaj, M., Fradet, L., Siegel, J., and Braatz, F., 2009, "Pressure Characteristics at the Stump/

Socket Interface in Transtibial Amputees Using an Adaptive Prosthetic Foot," Clin. Biomech., 24(10), 860-865).

Despite significant advances in prosthetic technology in recent years, commercially available lower limb prosthetic devices are as yet unable to provide biomimetic surface slope adaptation at the ankle on every step. Such examples may also include the BIOM (iWalk, Bedford, Mass., USA).

The prior art demonstrates that there is a current and long-felt need for an improved ankle prosthesis or ankle-foot prosthesis or orthosis that can better emulate the gait of an able-bodied individual and adapt to the terrain on the first step.

SUMMARY OF THE INVENTION

The invention provides prosthetic and orthotic ankle-foot systems. The systems can be used by a human subject as a prosthesis or an orthosis to assist the user's gait and to prevent or reduce the likelihood of compromising the user's balance.

In one embodiment the invention provides a self-adapting prosthetic system, the self-adapting prosthetic system comprising an adaptive ankle-foot prosthesis, a foot, means for attachment to a leg, the ankle foot prosthesis comprising a first torsion means, a second torsion means, and an engagement means, and wherein the first torsion means and the engagement means are in parallel and the second torsion means and the engagement means are in series. In a preferred embodiment, the first torsion means is in series with the second torsion means. In another preferred embodiment, the first torsion means comprises relatively low torsion and wherein the second torsion means comprises relatively high torsion. In a more preferred embodiment, the torsion means are selected from the group consisting of a spring, a tunable spring, a clockwork spring, a piston, a damper, a bumper, and an elastomeric material. In a yet more preferred embodiment, the engagement means is a clutch. In a most preferred embodiment, the clutch is selected from the group consisting of a friction clutch, a ball-and-socket triaxial friction clutch, and a wrap spring clutch. In a preferred embodiment, the engagement means comprises a displacement means, the displacement means selected from the group consisting of a shock-absorbing pylori, a hinge, a flexible member; a wrap spring, a rotatable collar, and a linkage means, the linkage means comprising a lever, a link, means for attaching the link to the means for attachment to a leg, means for attaching the link to the lever, means for attaching the lever to the pylori, means for attaching the lever to the wrap spring, wherein the means for attaching the lever to the wrap spring is selected from the group consisting of a string, a wire, a cable, a rod, a thread, a tape, a chain, a ribbon, a cord, a fiber, a line, and a filament, and wherein the means for attaching the lever to the wrap spring is a rotatable collar. In another preferred embodiment, the engagement means comprises a displacement means, the displacement means selected from the group consisting of a shock-absorbing pylori, a hinge, a flexible member; a wrap spring, and a linkage means, the linkage means comprising a lever, a first link, means for attaching the link to the means for attachment to a leg, means for attaching the link to the lever, means for attaching the lever to the foot, a second link means for attaching the lever to the wrap spring, wherein the wrap spring and the second linkage means are in series; and wherein the first torsion means and second torsion means both comprise an elastomeric material. In a more preferred embodiment, the link further comprises means for adjusting the length of said link. In a preferred embodiment, the self-adapting prosthetic system comprises a composition selected from the group consisting of stainless steel, copper, aluminum, titanium, metal matrix composite, metal alloy, NITI-NOL, DELRIN (acetal), acrylonitrile butadiene styrene (ABS), nylon, polypropylene, polybromate, polycarbonate, glycolised polyethylene terephthalate (8PETg) copolyester, polytetrafluorethylene (PTFE), ePTFE, polypropylene, a polymer, glass fiber-resin composites, and carbon fiber resin composites. In a preferred embodiment, a longitudinal orientation of the leg to the foot comprises a range of moveable contact relative to a surface. In a more preferred embodiment, the range of movable contact relative to a surface is a plantarflexion-dorsiflexion angle range of from between about 80° plantarflexion to about 45° dorsiflexion. In a preferred embodiment, the foot is a footplate. In another preferred embodiment, the foot is a foot shell.

In another preferred embodiment, the self-adapting prosthetic system comprises a housing arbor, a torque arbor, a low stiffness bumper, a high stiffness bumper, a neutralizing block, a housing base, a housing base socket, a housing base bar, a clutch spring, a clutch collar, a flexible connection means, and a torque transfer cap. In a preferred embodiment, the means for attachment to a leg are selected from the group consisting of a residual limb socket, direct skeletal attachment to the residual limb, and a leg cuff. In an additional preferred embodiment, wherein in use on an inclined surface, an ankle dorsiflexion angle increases compared to an ankle dorsiflexion angle in use of a level surface. In a more preferred embodiment, wherein in use on a declined surface, an ankle dorsiflexion angle decreases compared to an ankle dorsiflexion angle in use of a level surface. In a preferred embodiment, the adaptive ankle foot prosthesis is passive. In an additional preferred embodiment, the adaptive ankle foot prosthesis further comprises power means and wherein the adaptive ankle foot prosthesis is active. In a more preferred embodiment, the power means is selected from the group consisting of a motor, an actuator, a potentiometer, a force generator, a force sensor, and a battery.

In another preferred embodiment, the torsion means is selected from the group consisting of a spring, a tunable spring, a clockwork spring, a piston, a damper, a bumper, and an elastomeric material. In another preferred embodiment the neutralizing element and the clutch are in-line. In another most preferred embodiment, the ankle system has a plantarflexion-dorsiflexion range of from between 80° plantarflexion to about 45° dorsiflexion. In another embodiment the ankle system allows a user to emulate normal gait. In an alternative embodiment, the ankle system allows a user to approximately emulate normal gait.

In another preferred embodiment the self-adapting prosthetic system comprises a composition selected from the group consisting of stainless steel, copper, aluminum, titanium, metal matrix composite, metal alloy, NITINOL, DELRIN (acetal), acrylonitrile butadiene styrene (ABS), nylon, polypropylene, polybromate, polycarbonate, glycolised polyethylene terephthalate (PETg) copolyester, polytetrafluorethylene (PTFE), ePTFE, polypropylene, a polymer, glass fiber-resin composites, and carbon fiber resin composites. In an alternative embodiment the self-adapting prosthetic system further comprises a foot shell. In a preferred embodiment, the means for attachment to a leg are selected from the group consisting of a residual limb socket, direct skeletal attachment to the residual limb, and a leg cuff.

The invention also provides the self-adapting prosthetic system wherein in use for at least one gait cycle, the gait cycle comprising at least two phases of dorsiflexion over time, a load applied during a first phase of dorsiflexion results in the engagement means engaging, and wherein during the first phase when the velocity of ankle dorsiflexion angle equals zero the engagement means engages and dampens fully, and wherein removing the load during a second phase of dorsiflexion result in the engagement means disengaging and releasing fully.

In another embodiment the invention provides a self-adapting orthotic system, the self-adapting orthotic system comprising an adaptive ankle-foot orthosis, a foot, means for attachment to a leg, the ankle foot orthosis comprising a first torsion means, a second torsion means, and an engagement means, and wherein the first torsion means and engagement means are in parallel. In a preferred embodiment, the first torsion means comprises relatively low torsion and wherein the second torsion means comprises relatively high torsion. In an additional preferred embodiment, the torsion means are selected from the group consisting of a spring, a tunable spring, a clockwork spring, a piston, a damper, a bumper, and an elastomeric material. In an additional preferred embodiment, the engagement means is a clutch. In a more preferred embodiment, the clutch is selected from the group consisting of a friction clutch, a ball-and-socket triaxial friction clutch, and a wrap spring clutch. In an additional preferred embodiment, the engagement means comprises a displacement means, the displacement means selected from the group consisting of a hinge, a flexible member; a wrap spring, a rotatable collar, and a linkage means, the linkage means comprising a lever, a link, means for attaching the link to the means for attachment to a leg, means for attaching the link to the lever, means for attaching the lever to the pylori, means for attaching the lever to the wrap spring, wherein the means for attaching the lever to the wrap spring is selected from the group consisting of a string, a wire, a cable, a rod, a thread, a tape, a chain, a ribbon, a cord, a fiber, a line, and a filament, and wherein the means for attaching the lever to the wrap spring is a rotatable collar. In an additional preferred embodiment, the engagement means comprises a displacement means, the displacement means selected from the group consisting of, a hinge, a flexible member; a wrap spring, and a linkage means, the linkage means comprising a lever, a first link, means for attaching the link to the means for attachment to a leg, means for attaching the link to the lever, means for attaching the lever to the foot, a second link means for attaching the lever to the wrap spring, wherein the wrap spring and the second linkage means are in series; and wherein the first torsion means and second torsion means both comprise an elastomeric material. In a more preferred embodiment, the link further comprises means for adjusting the length of said link. In a preferred embodiment, the self-adapting orthotic system comprises a composition selected from the group consisting of stainless steel, copper, aluminum, titanium, metal matrix composite, metal alloy, NITINOL, DELRIN (acetal), acrylonitrile butadiene styrene (ABS), nylon, polypropylene, polybromate, polycarbonate, glycolised polyethylene terephthalate (8PETg) copolyester, polytetrafluorethylene (PTFE), ePTFE, polypropylene, a polymer, glass fiber-resin composites, and carbon fiber resin composites. In an additional preferred embodiment, a longitudinal orientation of the leg to the foot comprises a range of moveable contact relative to a surface. In a more preferred embodiment, the range of movable contact is a plantarflexion-dorsiflexion range of from between about 80° plantarflexion to about 45° dorsiflexion. In a preferred embodiment, the foot is a footplate. In an additional preferred embodiment, the foot is a foot shell. In an additional preferred embodiment, the self-adapting prosthetic system comprises a housing arbor, a torque arbor, a low stiffness bumper, a high stiffness bumper, a neutralizing block, a housing base, a housing base socket, a housing base bar, a clutch spring, a clutch collar, a flexible connection means, and a torque transfer cap. In a preferred embodiment, the means for attachment to a leg are selected from the group consisting of direct skeletal attachment to the limb, and a leg cuff. In an additional preferred embodiment, in use on an inclined surface, an ankle dorsiflexion angle increases compared to an ankle dorsiflexion angle in use of a level surface. In an additional preferred embodiment, in use on a declined surface, an ankle dorsiflexion angle decreases compared to an ankle dorsiflexion angle in use of a level surface. In a preferred embodiment, the adaptive ankle foot orthosis is passive. In an alternative preferred embodiment, the adaptive ankle foot orthosis further comprising power means and wherein the adaptive ankle foot orthosis is active. In a more preferred embodiment, the power means is selected from the group consisting of a motor, an actuator, a potentiometer, a force generator, a force sensor, and a battery.

In another preferred embodiment, the improved adaptive ankle-foot orthosis is shaped and adapted for placement on at least one side of the biological ankle of the user or individual. In another preferred embodiment, the torsion means is selected from the group consisting of a spring, a tunable spring, a clockwork spring, a piston, a damper, a bumper, and an elastomeric material. In another preferred embodiment the neutralizing element and the clutch are in-line. In another most preferred embodiment, the ankle system has a plantarflexion-dorsiflexion range of from between 80° plantarflexion to about 45° dorsiflexion. In another embodiment the ankle system allows a user to emulate normal gait. In an alternative embodiment, the ankle system allows a user to approximately emulate normal gait.

In a preferred embodiment, the means for attachment to an ankle are selected from the group consisting of direct skeletal attachment to the limb, a clamshell socket, and a leg cuff.

In another embodiment, the invention provides a prosthetic or orthotic system for a user to emulate normal gait, the prosthetic system comprising an ankle member, the ankle member comprising a reversible engagement means, a first torsion means, and a joint, and wherein in use, a torsion curve plot of ankle moment against ankle dorsiflexion angle of the prosthetic system during a gait cycle comprises at least one transition point, wherein the reversible engagement means is operatively connected to the first torsion means, wherein the first torsion means is operatively connected to the joint, and wherein the joint is operatively connected to the engagement means. In an alternative embodiment, the system allows a user to approximately emulate normal gait. In a preferred embodiment the system is used by a user to proceed over a surface without compromising balance wherein the surface comprises a plurality of grades or elevations. In a most preferred embodiment the prosthetic system automatically adapts to different surface conditions. In an alternative embodiment the self-adapting prosthetic or orthotic system further comprises a foot shell.

The invention also provides the self-adapting orthotic system wherein in use for at least one gait cycle, the gait cycle comprising at least two phases of dorsiflexion over time, a load applied during a first phase of dorsiflexion results in the engagement means engaging, and wherein during the first phase when the velocity of ankle dorsiflexion angle equals zero the engagement means engages and dampens fully, and wherein removing the load during a second phase of dorsiflexion result in the engagement means disengaging and releasing fully.

The invention also provides a method for providing essentially normal gait in an amputee, the amputee having lost a lower limb extremity, the method comprising (i) providing the self-adapting ankle-foot prosthetic system disclosed herein; (ii) attaching the self-adapting ankle-foot prosthetic system to the lower limb of the amputee; (iii) allowing the amputee to ambulate for at least one gait cycle, the gait cycle comprising at least two phases of dorsiflexion over time, (iv) applying a load during a first phase of dorsiflexion and resulting in the engagement means engaging, wherein during the first phase when the velocity of ankle dorsiflexion angle equals zero the engagement means engages and dampens fully, and wherein removing the load during a second phase of dorsiflexion the engagement means disengages and releases fully, the method resulting in providing essentially normal gait to the amputee. In a preferred embodiment, the gait cycle comprises at least three phases of ankle flexion. In another preferred embodiment, the engagement of the engagement means coincides with a first transition point of the torsion curve plot. In an additional preferred embodiment, the disengagement and release of the engagement means coincides with a second transition point of the torsion curve plot. In another embodiment, the method further comprises a step of determining an equilibrium point, wherein the equilibrium point of the torsion curve plot is at a negative dorsiflexion angle. In an additional preferred embodiment, the method further comprises a step of determining an equilibrium point, wherein the equilibrium point of the torsion curve plot is at a positive dorsiflexion angle.

The invention also provides a method for providing essentially normal gait in a subject having a disability affecting the lower limb, the method comprising (i) providing the self-adapting ankle-foot orthotic system disclosed herein; (ii) attaching the self-adapting ankle-foot orthtic system to the lower limb of the subject; (iii) allowing the subject to ambulate for at least one gait cycle, the gait cycle comprising at least two phases of dorsiflexion over time, (iv) applying a load during a first phase of dorsiflexion and resulting in the engagement means engaging, wherein during the first phase when the velocity of ankle dorsiflexion angle equals zero the engagement means engages and dampens fully, and wherein removing the load during a second phase of dorsiflexion the engagement means disengages and releases fully, the method resulting in providing essentially normal gait to the subject. In a preferred embodiment, the gait cycle comprises at least three phases of ankle flexion. In an alternative preferred embodiment, the engagement of the engagement means coincides with a first transition point of the torsion curve plot. In an additional preferred embodiment, the disengagement and release of the engagement means coincides with a second transition point of the torsion curve plot. In another embodiment, the method further comprises a step of determining an equilibrium point, wherein the equilibrium point of the torsion curve plot is at a negative dorsiflexion angle. In an additional preferred embodiment, the method further comprises a step of determining an equilibrium point, wherein the equilibrium point of the torsion curve plot is at a positive dorsiflexion angle.

The ankle-foot devices disclosed herein automatically adapt to various walking surfaces using stiffness-based control and few or no sensing devices. This mode of control may be preferable to damping-based control (Koniuk, 2002, supra) because it allows for return of stored energy. In theory, equilibrium-point prosthetic ankle-foot devices of the invention are designed to store and return energy with a high degree of efficiency.

BRIEF DESCRIPTION OF THE DRAWINGS

FIG. 12 illustrates an exemplary structural grouping of the second design iteration.

FIG. 13 illustrates the positioning of the low stiffness bumper (11) and high stiffness bumper (12) within the intermediate structure (16).

FIG. 14 illustrates an exemplary design of the wrap spring clutch (14).

FIG. 15 illustrates various elements used to create one embodiment of the invention.

DETAILED DESCRIPTION OF THE INVENTION

Figure 1:
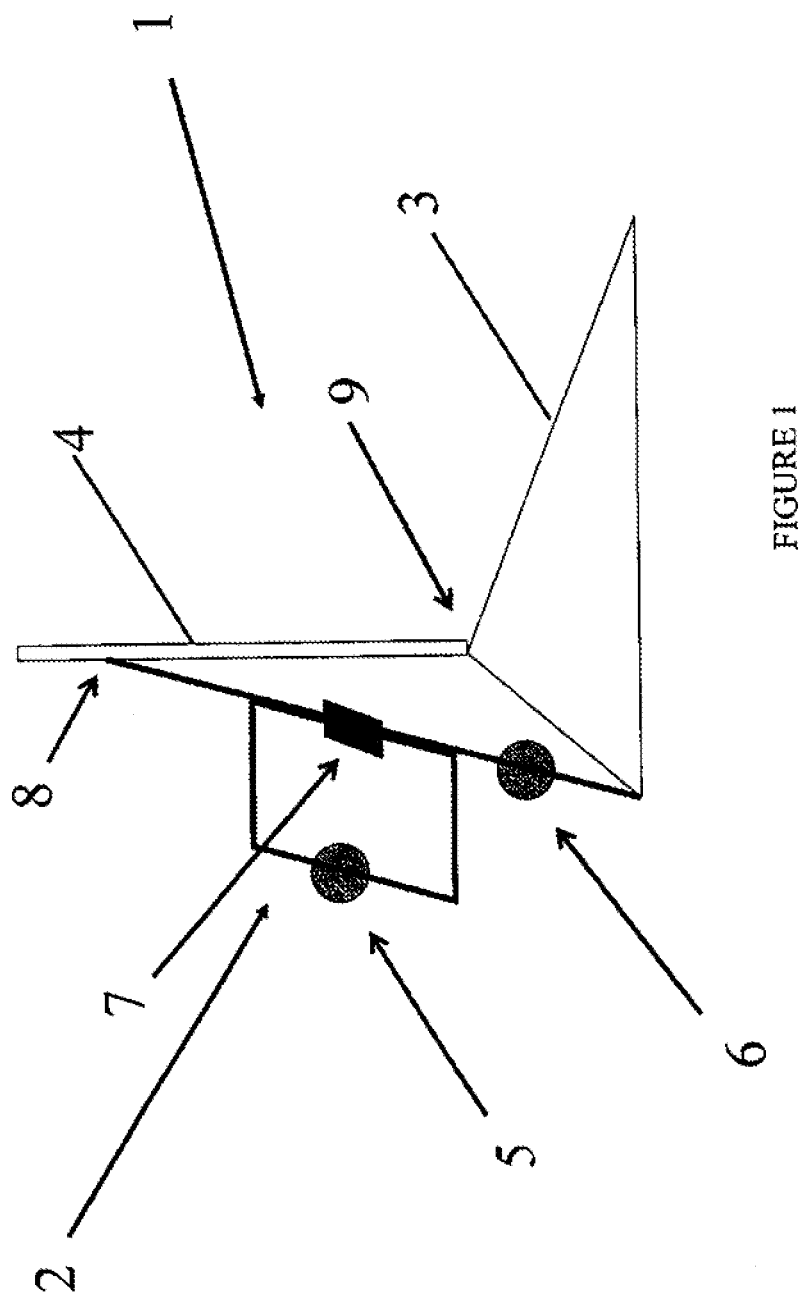
FIG. 1 illustrates an exemplary embodiment of the invention.

The embodiments disclosed in this document are illustrative and exemplary and are not meant to limit the invention. Other embodiments can be utilized and structural changes can be made without departing from the scope of the claims of the present invention.

As used herein and in the appended claims, the singular forms "a," "an," and "the" include plural reference unless the context clearly dictates otherwise. Thus, for example, a reference to "a residue" includes a plurality of such residues, and a reference to "a torsion means" is a reference to one or more torsion means and equivalents thereof, and so forth. In addition, the term "torsion means" is taken to be equivalent to "stiffness means" and to "impedance" and the terms are interchangeable as disclosed herein.

The system described herein provides improvements to the inventors' prior art invention. The inventors were under obligation at the time all the inventions were made to assign the rights to the same entities. The prior invention demonstrated slope adaptation but was prone to wear, breakage, and noise production (Williams R J, Hansen A H, Gard S A. (2009) Prosthetic Ankle-Foot Mechanism Capable of Automatic Adaptation to the Walking Surface. Journal of Biomechanical Engineering, Vol., 131, No. 3, 035002). The ability of the improved system disclosed hereinto adapt to surface slopes was evaluated by conducting a pilot study to compare the ankle moment-angle curves from the adaptable ankle prototype (FIG. 7 and FIG. 8) to the subjects' usual prostheses.

Previous work suggested that the dominant change at the ankle when walking on sloped surfaces is realignment of the effective prosthetic ankle-foot rocker (called the ankle-foot roll-over shape) about the ankle axis, while the roll-over shape itself remained relatively constant (Hansen, A., Childress, D., and Miff, S., 2004, "Roll-Over Characteristics of Human Walking on Inclined Surfaces," Hum. Mov. Sci., 23(6): 807-821). The rotation of the roll-over shape corresponds to a change in effective alignment of the ankle, or a change in equilibrium point.

During level ground walking at self-selected walking speeds, the able-bodied ankle moment-angle curves show essentially two different sloped regions (Hansen, A., Childress, D., Miff, S., Gard, S., and Mesplay, K., 2004, "The Human Ankle During Walking: Implications for Design of Biomimetic Ankle Prostheses," J. Biomech., 37(10): 1467-1474). One region has a low slope and occurs during early stance, whereas the other region appears to have a much greater slope and occurs as the person rolls over their stance foot. The slope of the ankle moment-angle curve corresponds to "quasi-stiffness" (Latash, M., and Zatsiorsky, V., 1993, "Joint Stiffness: Myth or Reality?" Hum. Mov. Sci., 12: 653-692). The two different quasi-stiffnesses could be obtained by viscoelastic bumpers with a mechanism to switch between the bumpers.

To achieve two rotational quasi-stiffnesses, a system was developed that placed the low and high stiffness bumpers in series with one another. This is in contrast to the placement and relationship of the various torsion or stiffness means and the engagement means of the previous invention and of the prior art. A clutch prevented compression of the low stiffness bumper when the device was loaded and the foot was rotated in the direction of dorsiflexion (FIGS. 2 and 3), forcing deflection to occur at the high stiffness bumper, and beginning at potentially any ankle angle. This deflection could begin in some amount of plantarflexion (walking on declines to slight inclines) or dorsiflexion (walking on steep inclines). The system illustrated in FIG. 3 is identical to that of FIG. 2 except comprising two first torsion means (5).

Figure 2:
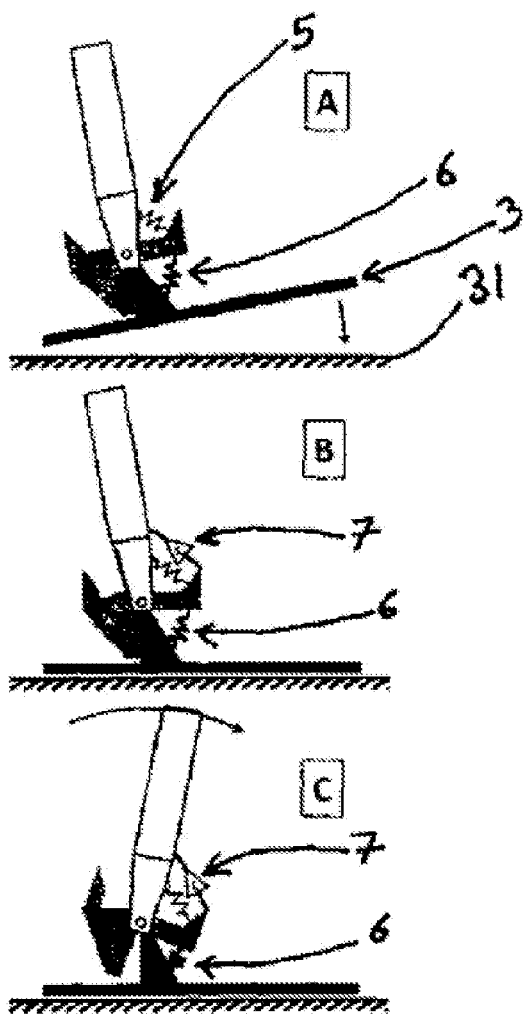
FIG. 2 illustrates an exemplary model of an adaptable ankle system.
Figure 3:
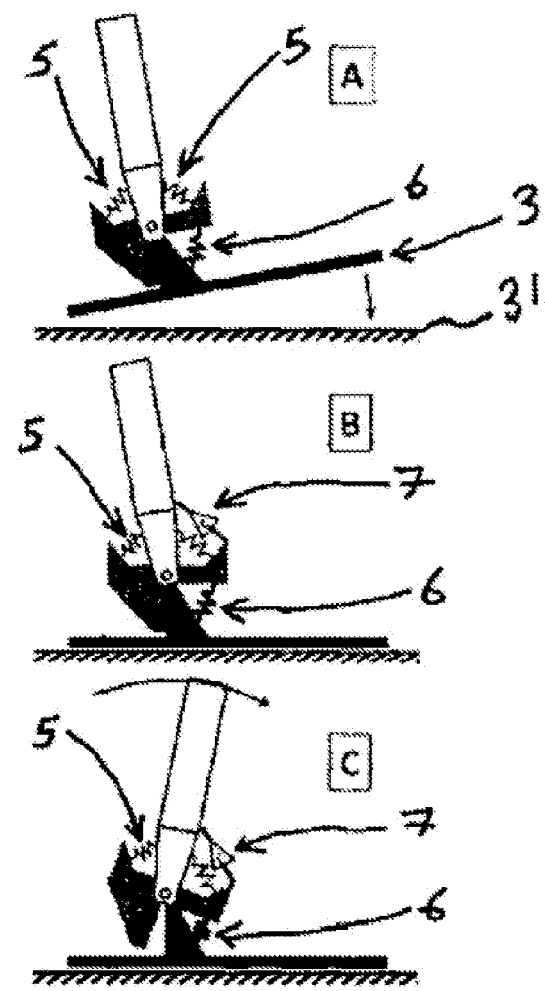
FIG. 3 illustrates an alternative exemplary model of an adaptable ankle system with an additional torsion means, loading sequence as in FIG. 2.

The stiffness elements act through an intermediate structure (represented in dark gray in FIGS. 2 and 3) that can be effectively locked to the shank when the clutch is engaged, bypassing the low stiffness element and setting the neutral point of the high stiffness element (FIGS. 2B and 3B). Further angular deflection of the device in the direction of dorsiflexion (FIGS. 2C and 3C) results in compression of the high stiffness element, providing support as the user rolls over their ankle. This approach produces a system that is realigned for the surface on every step because the neutral point of the high stiffness element is determined on every step after the prosthetic ankle mechanism has realigned to the walking surface.

Adaptation to sloped surfaces can be demonstrated by measuring the ankle moment-angle curves (FIG. 5) when walking on surfaces with different slopes. Translation of the ankle moment-angle curves along the ankle angle axis indicates a different equilibrium point, or set point (ankle angle at which there is zero net ankle moment, FIG. 6C), essentially indicating a different alignment of the prosthesis. Our proof-of-concept prototype demonstrated lateral shifting of the ankle moment-angle curves when walking on five different slopes, while a non-adaptable ankle showed no shifting of moment-angle curves for the different slopes (Nickel, E., Hansen, A., and Gard S., 2011 "Prosthetic Ankle-Foot System That Adapts to Sloped Surfaces" J. Med. Devices 5: 027519).

The clutch used to lock out the low stiffness bumper in dorsiflexion needed to be small and light enough to fit within the reasonable dimensions of an anatomical ankle and foot, while still being capable of withstanding specific ankle moments of approximately 1.7 N*m/kg (based on data from Hansen et al. 2004 supra). For a 100 kg person, this would result in an ankle moment of 1700 N*m. During steady state walking, the clutch would be required to resist an external dorsiflexion moment only, thus a unidirectional clutch, such as the wrap spring clutch, would be acceptable.

Wrap spring clutch mechanisms have been used in other rehabilitation applications due to the relatively large moment resistance such a mechanism can provide relative to the size and weight of the clutch system (Wiebusch, C., 1939, "The Spring Clutch," J. App. Mech., pp. 103-108). The application of wrap spring clutches to prosthetics and orthotics has thus far been primarily in upper limb prosthetic components and orthotic knee joints (Kangude, A., Burgstahler, B., Kakastys, J., and Durfee, W., 2009, "Single Channel Hybrid FES Gait System Using an Energy Storing Orthosis: Preliminary Design," Proc. IEEE Eng. Med. Bio. Soc., pp. 6798-6801; Irby, S. E., Kaufman, K. R., Wirta, R. W., and Sutherland, D. H., 1999, "Optimization and Application of a Wrap-Spring Clutch to a Dynamic Knee-Ankle-Foot Orthosis," IEEE Trans. Rehabil. Eng., 7(2), pp. 130-134).

The exemplary clutch spring used for the present system was the drive spring of a Warner Electric CB-7 clutch-brake system, rated for 1700 N*m. Due to the size and mass of the commercial clutch system, only the spring was used for this application. The clutch arbors were custom fabricated from 2024 high strength aluminum alloy.

The adaptable ankle model presented in FIG. 2 and FIG. 3 may comprise three elements, a shank, an intermediate element, and a foot. The shank structure (white structures in FIG. 2 or FIG. 3) interfaced the adaptable ankle with the subject's socket and transferred moments to the driving arbor of the wrap spring clutch. The intermediate structure (gray structures in FIG. 2 or FIG. 3) received moments from the driven arbor of the wrap spring clutch, formed a track within which the left side of the shank structure rested, and applied forces to the high stiffness bumper. The foot structure (black structures in FIG. 2 or FIG. 3) supported the shaft about which all structures rotated, supported the high stiffness bumper, and held the footplate.

Figure 7:
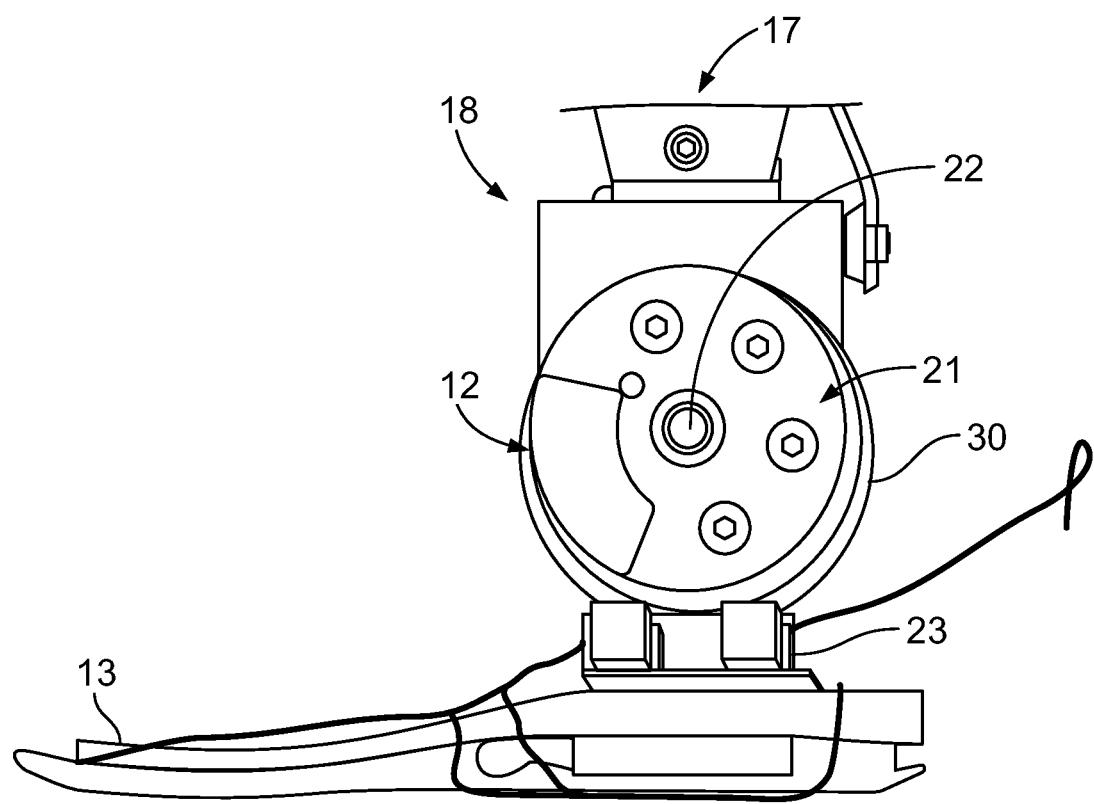
FIG. 7 illustrates an exemplary embodiment of an adaptable ankle in side view of the high stiffness bumper with the socket side of the base structure removed.

Between the intermediate structure and the foot structure rested the high stiffness bumper (FIG. 7). It was made from nominally 90 Shore A durometer polyurethane rubber (samples measured at approximately 110 Shore A). The rubber bumper rested in a socket in one side of the base structure with the top of the bumper resting against one part of the intermediate structure while the bottom of the bumper rested against a rib that protruded from the base structure wall. This bumper was compressed until the ankle achieved a dorsiflexion angle of approximately 15 degrees, at which time the shank structure physically rested against the socket side of the foot structure (bottomed out).

Between the shank structure and the intermediate structure rested the low stiffness bumpers. These bumpers were intended to neutralize the orientation of the footplate during swing, when the prosthesis was unloaded. To achieve this neutralization, the bumpers were cast as modular sections from Oomoo 30, a silicone rubber from Smooth-On with a nominal durometer of 30 Shore A at full cure. These bumpers were assembled in the interior space of the wrap spring clutch arbors. Each arbor had a block bolted inside. The bumpers filled the space between these "neutralizing" blocks such that when one arbor rotated with respect to the other, one of the bumpers was being compressed. This arrangement provided neutralization during swing and low stiffness in both plantarflexion and dorsiflexion during early stance when the prototype "finds" the surface.

Figure 8:
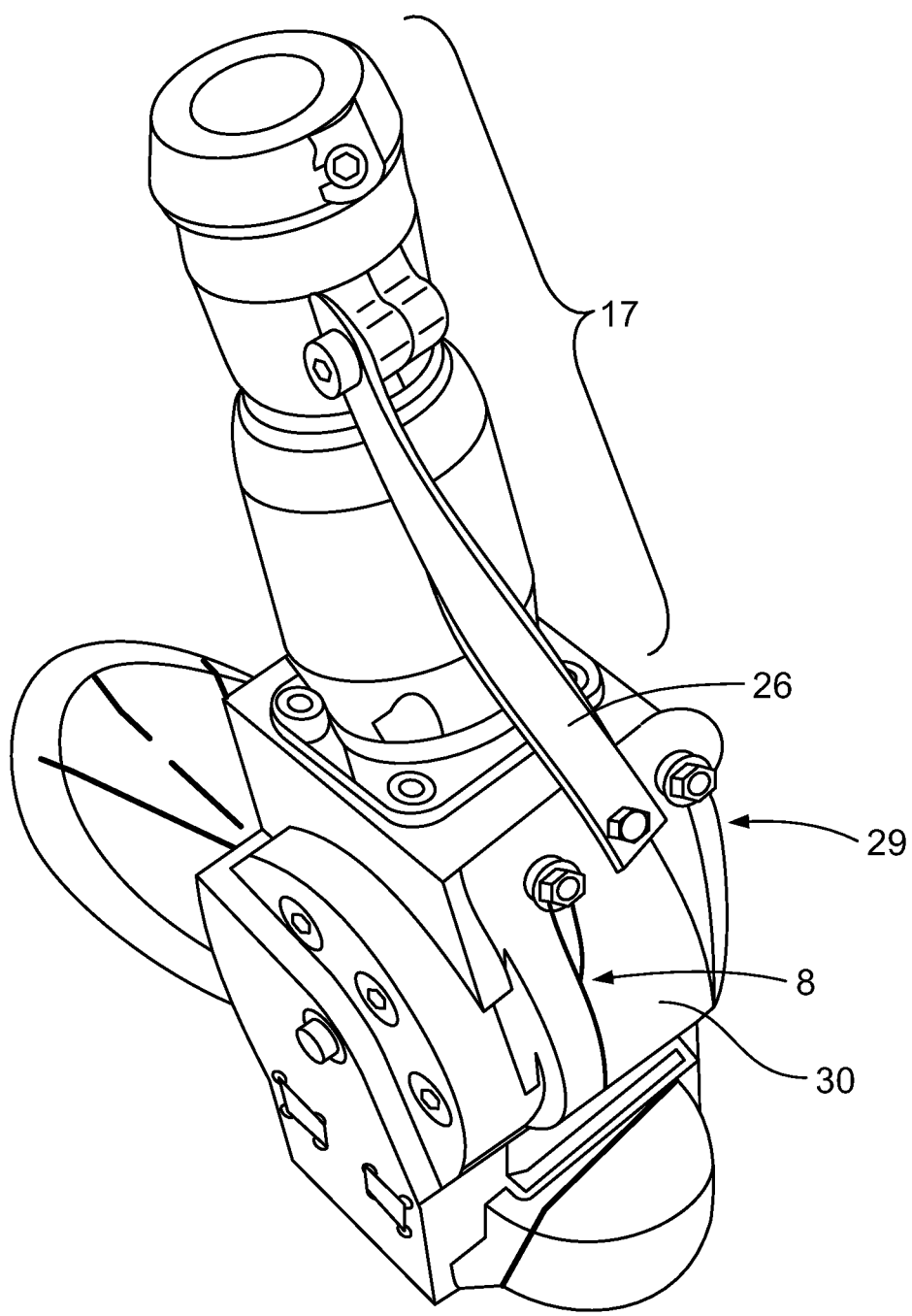
FIG. 8 illustrates an exemplary engagement mechanism of the adaptable ankle.

The operation of the adaptable ankle required that the clutch be engaged and disengaged at different phases of the gait cycle. Upon being loaded by the user, the clutch must be engaged to resist externally applied dorsiflexion moments, whereas upon being unloaded the clutch must be disengaged to permit neutralization. Therefore a commercially available shock absorbing pylori (Endolite Telescopic-Torsion Pylori) was used to provide a load-based deflection that could be utilized to engage the clutch (FIG. 8). The displacement at the shock absorbing pylori was amplified by a linkage with an approximate gain of two.

When the prototype was unloaded, the shock absorbing pylori would be at full extension. In full extension, the end of the wrap spring was being lifted away from the arbors, resulting in disengagement. As the pylori received load, the shock absorbing pylori compressed and the descending link (FIG. 8) moved downward, permitting the lever to rotate downward, releasing tension on the string. The string was affixed to the control collar (30, FIG. 7). The resting interior diameter of the clutch spring was smaller than the outer diameter of the arbors, thus when under no external influence, the clutch spring would rest against the arbors. When the control collar was rotated by the lever pulling up on the string, the end of the clutch spring was rotated in a direction that would cause an increase in the interior diameter of the clutch spring, preventing the coil from gripping the arbors and therefore disengaging the clutch. Thus the clutch was disengaged during swing, permitting neutralization.

Improvements of the Invention Over Existing Technologies

The improvements over existing technologies include the ability to adapt to various shoe heel heights and walking inclinations and the provision for plantarflexion at late stance. The device may prove to be superior in energy storing and release characteristics over existing devices although this remains to be seen. Koniuk (2002, supra) has stated the claim of adaptation to shoe heel height and walking inclination in a recently patented design that utilizes damping-control. Our design differs from Koniuk's (2002) in that it utilizes stiffness control and biomimetic foot roll-over shape, allowing the device to achieve an ankle-foot roll-over shape similar to that of an able-bodied person's ankle-foot system during walking, while also allowing for energy return and plantarflexion in late stance.

Design and Manufacture of the Invention

This design is realized in a number of ways. Rotational springs, linear springs, or combinations of the two are used to supply the appropriate impedances about the ankle at different stages of the walking cycle. In the following diagrams, however, the concept of the device will be illustrated using linear springs to describe an "equilibrium-point" prosthetic ankle joint.

FIG. 1 is an exemplary diagram of the device pointing out the various components of the device.

FIG. 2 illustrates an exemplary model of an adaptable ankle system. During early loading, the clutch is disengaged and the low stiffness element dominates (A). Upon reaching "foot flat" and sufficient loading (B), the wrap spring clutch (triangle "c") is engaged, transferring displacement in the direction of dorsiflexion (C) to the high stiffness element, bypassing the low stiffness element.

FIG. 3 illustrates an alternative exemplary model of an adaptable ankle system with an additional first torsion means; loading sequence as in FIG. 2.

Figure 4:
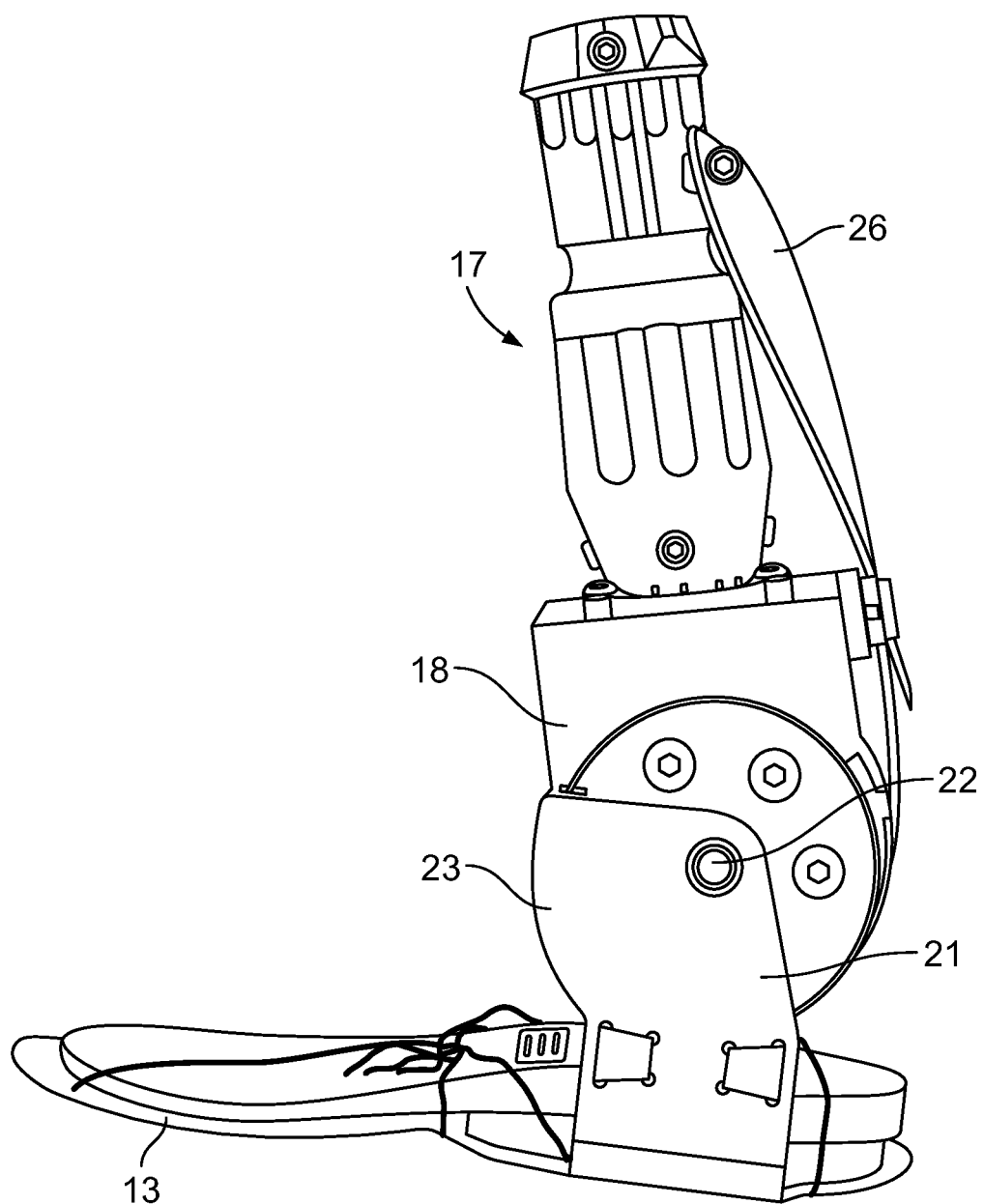
FIG. 4 illustrates an exemplary adaptable ankle system.

FIG. 4 illustrates an exemplary adaptable ankle system.

Figure 5:
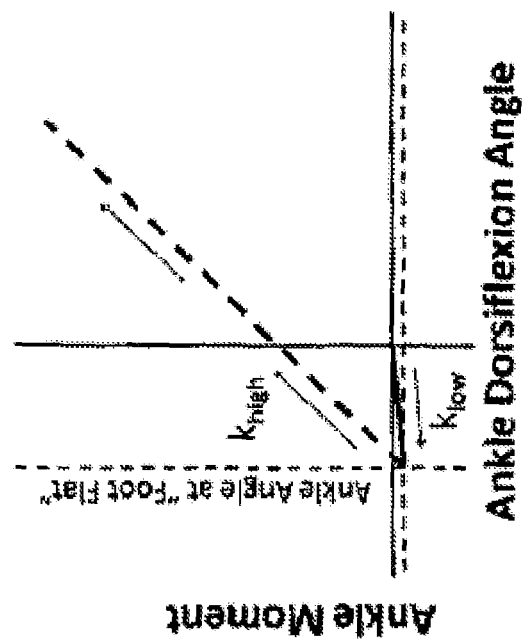
FIG. 5 illustrates the theoretical function of the stiffness elements.

FIG. 5 illustrates the theoretical function of the stiffness elements. The series combination of the low and high stiffness elements has a low slope ($k_{low}$) on the ankle moment-angle curve and is generally deflected in plantarflexion during early stance. The high stiffness element has a greater slope ($k_{high}$) and is only compressed when the wrap-spring clutch is engaged and the ankle moves in the direction of dorsiflexion.

Figure 6:
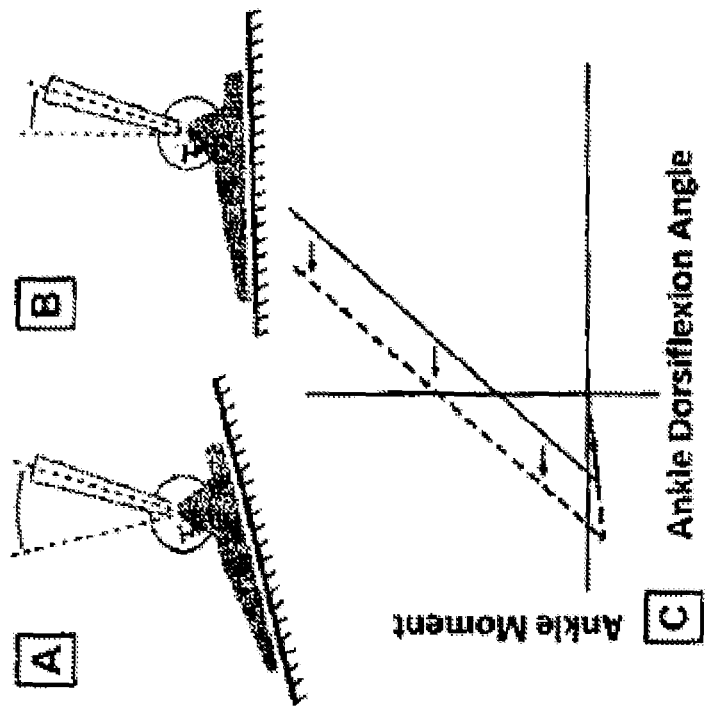
FIG. 6 illustrates further the theoretical function of the stiffness elements.

FIG. 6 illustrates further the theoretical function of the stiffness elements: as the adaptable ankle adapts to the surface slope, the low stiffness elements are compressed based on the ankle angle at foot flat (A and B). Thus the high stiffness element would begin to be compressed at different ankle angles dependent on the surface slope. The point on the ankle moment-angle plot in the high stiffness region where the net ankle moment is zero (no net moment being applied to the user) is referred to as the 'equilibrium point" and is expected to shift along the ankle axis for surfaces of different slopes (C).

FIG. 7 illustrates an exemplary embodiment of an adaptable ankle in side view of the high stiffness bumper with the socket side of the base structure removed. The high stiffness bumper and torque transfer cap rested within the socket. The torque transfer cap pressed down on the top of the bumper when loaded, while the bottom of the bumper rested against a rib projecting from the socket wall.

FIG. 8 illustrates an exemplary engagement mechanism of the adaptable ankle. When unloaded, the linkage pulled up on the string to rotate the control collar of the wrap spring clutch, forcing the clutch to be disengaged. When loaded, the shock absorbing pylori compressed, propagating displacement through the linkage such that the clutch spring was permitted to engage, effectively locking the shank and intermediate structures together against motion in the direction of dorsiflexion. The ability to rotate was blocked out of the shock absorbing pylori.

Figure 9:
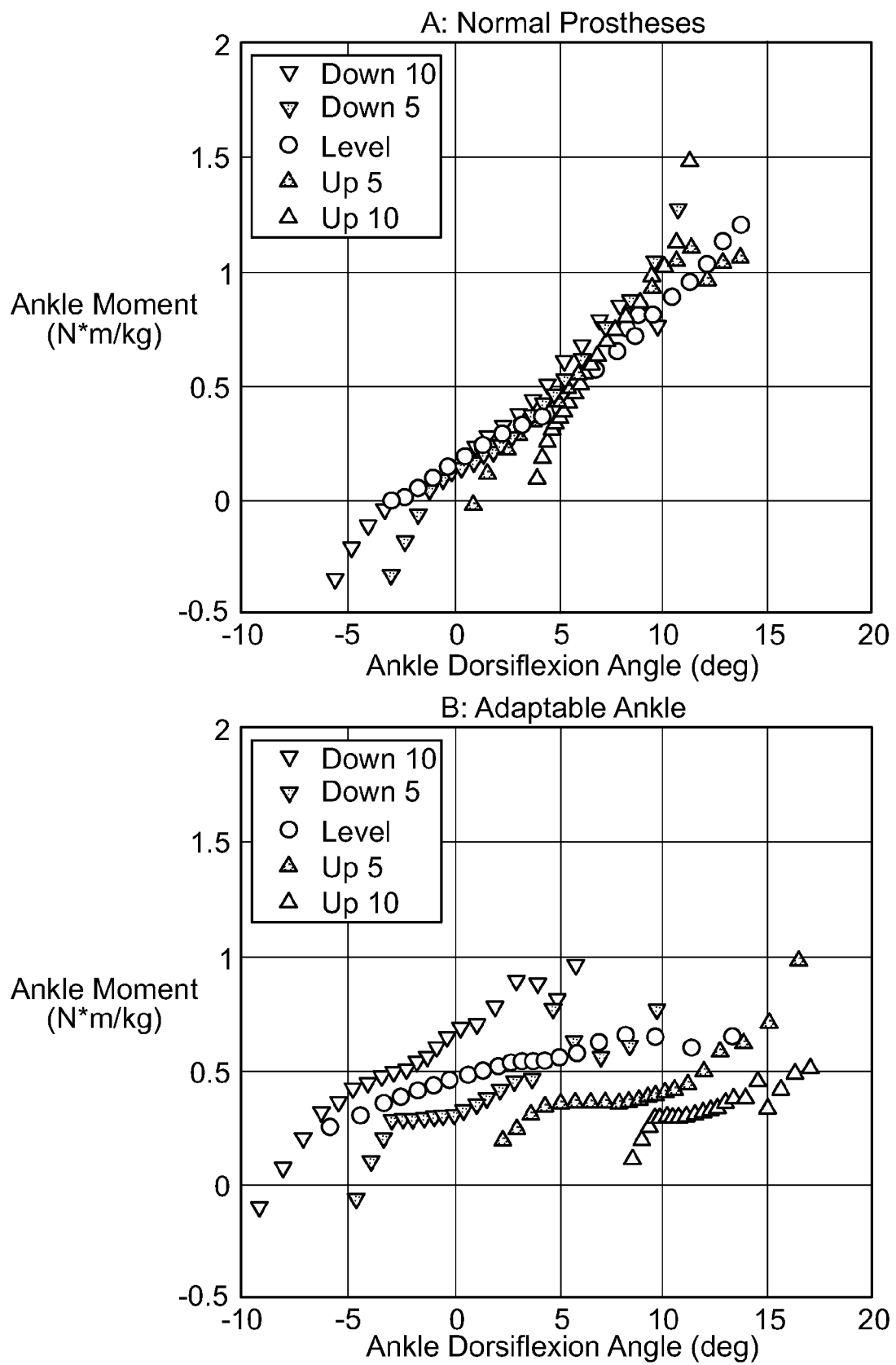
FIG. 9 illustrates plots of mean ankle moment vs. ankle angle during single-limb support for the subjects tested.

FIG. 9 illustrates plots of mean ankle moment vs. ankle angle during single-limb support for the subjects tested (n=3) using their usual prostheses (A) or the adaptable ankle prototype (B). The translation of the moment-angle curves when using the adaptable ankle prototype suggests the prototype was changing set-point on sloped surfaces. The lower slope indicates the adaptable ankle was also less stiff than the subjects' usual prostheses. One subject had plateaus when using the adaptable ankle prototype, suggesting the clutch may have been slipping, possibly due to miscalibration of the engagement mechanism.

The springs are chosen to replicate impedance values found for able-bodied human walking (Hansen et al., (2004b) "The Human Ankle During Walking: Implications for Design of Biomimetic Ankle Prostheses and Orthoses" J. Biomech. 37: 1467-1474). These values change somewhat with walking speed but will be designed based on slow to normal walking speeds. The characteristics for extremely fast walking speeds cannot be mimicked exactly using a passive system (Hansen et al., 2004b, supra).

Figure 10:
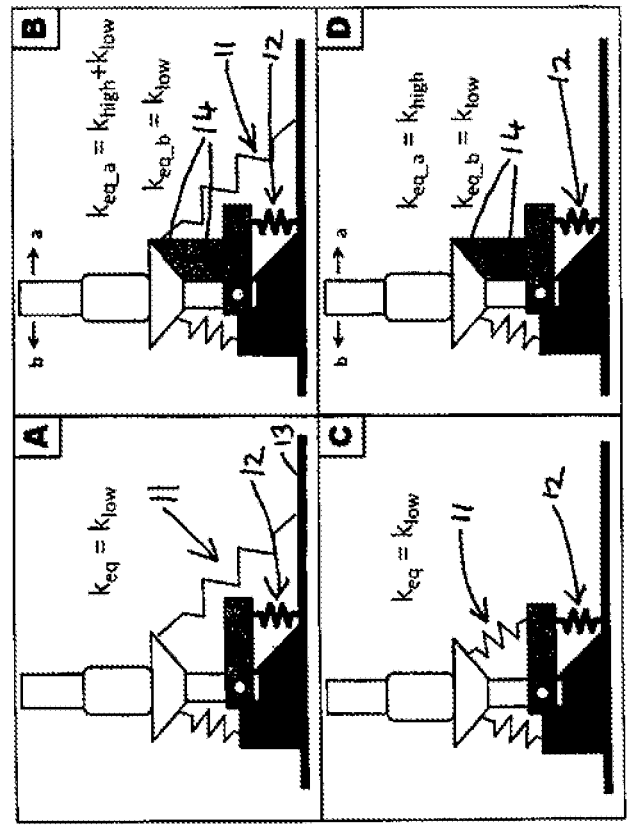
FIG. 10 illustrates mechanical modes of effective stiffness elements for two exemplary design iterations.

FIG. 10 illustrates mechanical modes of effective stiffness elements for two exemplary design iterations. The first design iteration (FIGS. 10 A and B) have a low stiffness element (11) in parallel with a high stiffness element (12). Hence, when the clutch was not engaged (illustrated by absence of clutch on FIG. 10 A) the low stiffness element (11) dominated (effective ankle rotation stiffness ($k_{eq}$)=low stiffness ($k_{low}$), whereas when the clutch (14) was engaged (illustrated by presence of clutch on FIG. 10B) dorsiflexion displacements (a) engaged the clutch, engaging both stiffness elements (11 and 12) (dorsiflexion effective ankle rotation stiffness ($k_{eq\_}$ $_a$)=high stiffness ($k_{high}$)+low stiffness ($k_{low}$), while platarflexion displacements (b) only engaged the low stiffness element (11) (plantarflexion effective ankle rotation stiffness ($k_{eq\_b}$)=low stiffness ($k_{low}$).

The second design iteration (FIGS. 10C and D) moved the low stiffness element (11) inside the device, thereby placing it in series with the high stiffness element (12). When the clutch was not engaged (illustrated by absence of clutch on FIG. 10C), the low stiffness element (11) dominated ($k_{eq}$=($k_{low}$), whereas when the clutch (14) was engaged (illustrated by presence of clutch on FIG. 10D) dorsiflextion displacements engaged only the high stiffness element (12) ($k_{eq\_a}$=($k_{high}$) and plantarflexion displacements engaged only the low stiffness element (11) ($k_{eq\_b}$=($k_{low}$).

Figure 11:
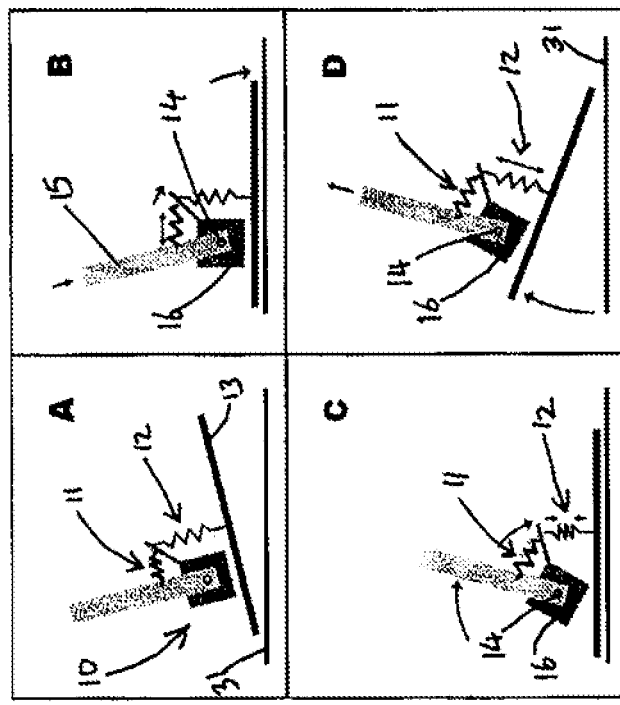
FIG. 11 illustrates a conceptual diagram of the adaptable ankle function.

FIG. 11 illustrates a conceptual diagram of the adaptable ankle function of the second design iteration in use by a subject. FIG. 11A: the adaptable ankle (10) is in a neutral state at initial contact with a surface (31), the low (11) and high stiffness (12) bumpers in series, thus the low stiffness bumper dominates the system. FIG. 11B: as the foot is loaded (arrows down) the ankle plantarflexes such that the footplate (13) rests against the surface (31). The low stiffness bumpers (11) absorb the deflection and are in a stressed state and the clutch (14) locks the shank structure (light grey, 15) to the intermediate structure (dark grey, 16). FIG. 11C: as the subject rolls over (arrows) the adaptable ankle the shank (15) and intermediate (16) structures rotate together due to the action of the clutch (14) compressing the high stiffness bumper (12). FIG. 11D: as the adaptable ankle is unloaded (arrows up) the high stiffness bumper (12) returns stored energy until the clutch (14) disengages. When the clutch disengages the entire system returns to neutral, as shown in FIG. 11A.

FIG. 12 illustrates an exemplary structural grouping of the second design iteration. The pylori (17), housing (18), and housing arbor (19) comprised the housing or shank structure (FIG. 12A, 15); the torque arbor (20) and torque transfer cap (21) comprised the intermediate structure (FIG. 12B, 16); the shaft (22), footplate (13), and both parts of the housing base (23) comprised the foot structure (FIG. 12C, 3). The torsion means are not shown.

FIG. 13 illustrates the positioning of the low stiffness bumper (11) and high stiffness bumper (12) within the intermediate structure (16). FIG. 13A shows the assembled structure. FIG. 13B shows an exploded view of the structure.

FIG. 14 illustrates an exemplary design of a clutch (14) comprising a wrap spring coil (24) positioned around the intermediate structure (16) in two views. Also shown are a control tang (27) to which a linkage may be connected, and a locking tang, (28) that engages with a recess in the intermediate structure.

FIG. 15 illustrates an exemplary exploded view of the components of the adaptable ankle system.

Figure 16:
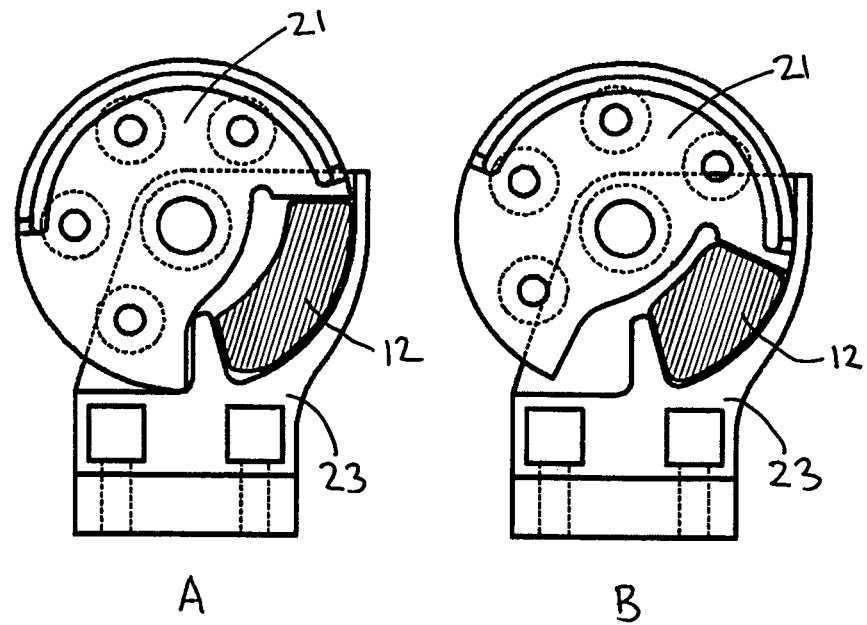
FIG. 16 illustrates an exemplary arrangement of the high stiffness means.

FIG. 16 illustrates an exemplary arrangement of the high stiffness means showing the high stiffness means (12) uncompressed (A) or compressed (B) in a view from the housing arbor towards the housing base.

Figure 17:
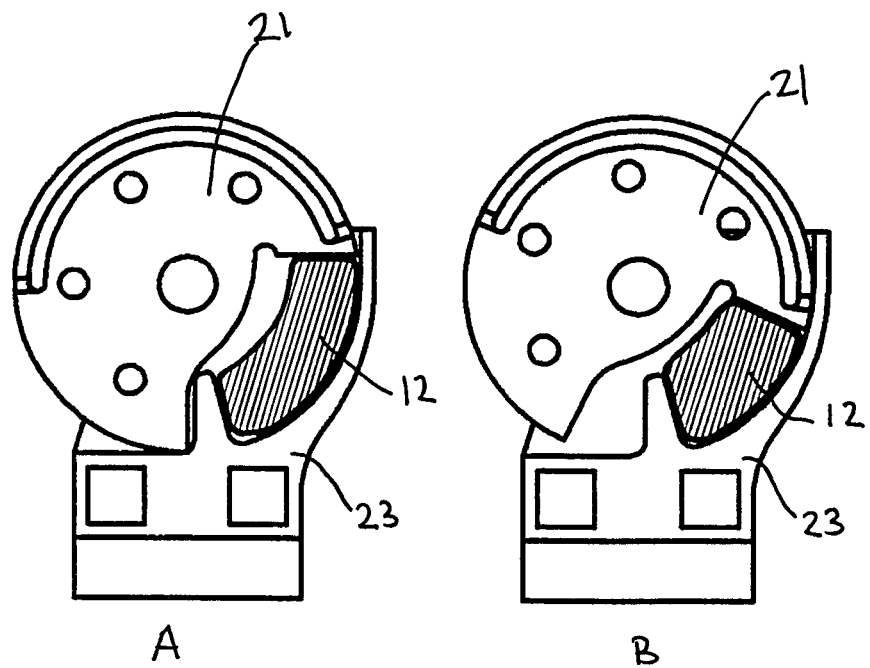
FIG. 17 illustrates an exemplary arrangement of the high stiffness means.

FIG. 17 illustrates an exemplary arrangement of the high stiffness means showing the high stiffness means (12) uncompressed (A) or compressed (B) in a view from the housing arbor towards the housing base, partially hidden by the torque transfer cap.

Figures 18, 19:
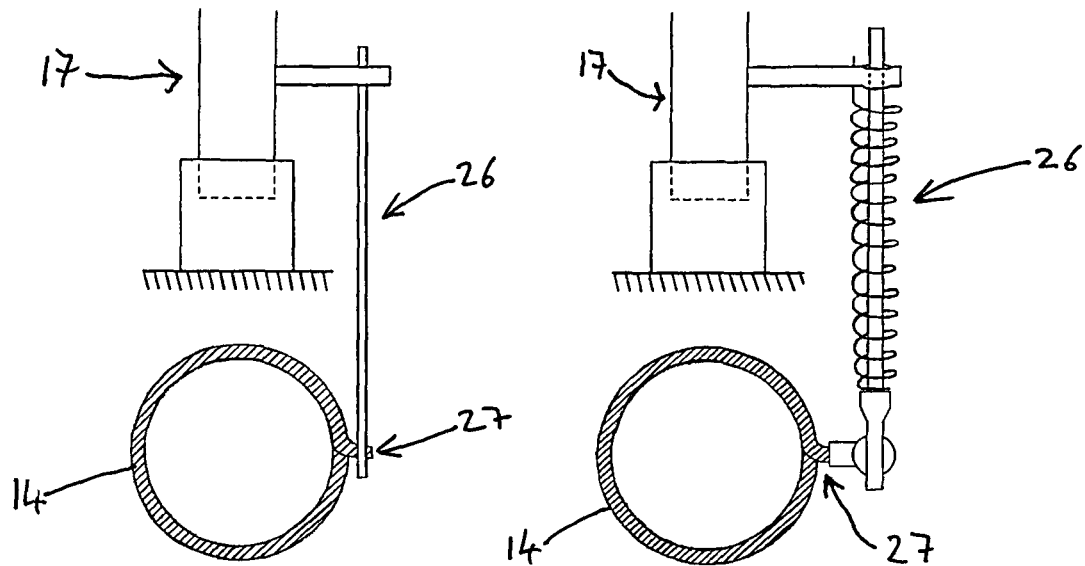
FIGS. 18 through 20 illustrate exemplary fully assembled linkage means for engaging or disengaging the clutch.
Figure 20:
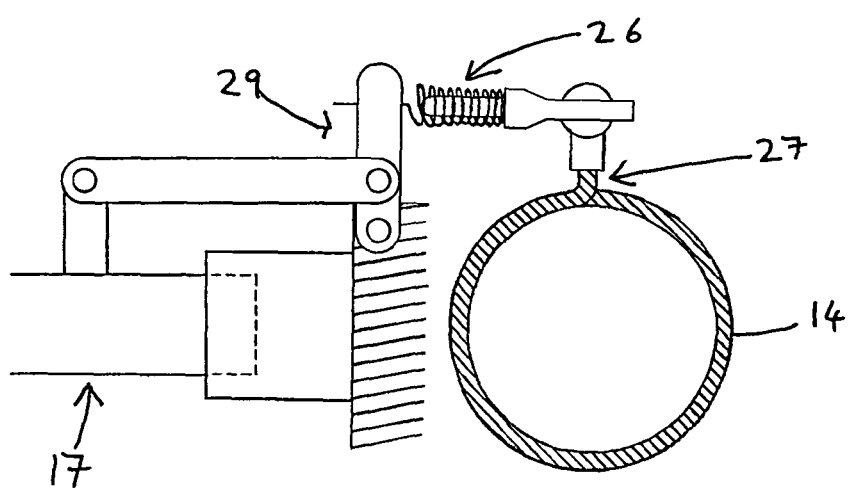

FIGS. 18 through 20 illustrate exemplary linkage means (26) for engaging or disengaging the clutch (14).

Exemplary Embodiments of the Invention

In one preferred embodiment, the ankle system has a plantarflexion-dorsiflexion range of from between 80° plantarflexion to about 45° dorsiflexion. For example, the range of plantarflexion can be >0°, 5°, 10°, 15°, 20°, 25°, 30°, 35°, 40°, 45°, 50°, 55°, 60°, 65°, 70°, 75°, and 80° and any angle therebetween. In another example, the range of dorsiflexion can be >0°, 1°, 2°, 3°, 4°, 5°, 6°, 7°, 8°, 9°, 10°, 11°, 12°, 13°, 14°, 15°, 16°, 17°, 18°, 19°, 20°, 25°, 30°, 35°, 40°, and 45° and any angle therebetween. Where there is neither plantarflexion nor dorsiflexion the ankle system is at 0°, neutral.

The expected commercial applications include ankle-foot prostheses and orthoses for persons with disabilities. These components would hopefully improve the mobility of these persons by allowing them to automatically adapt to various walking surfaces while at the same time giving them biomimetic ankle-foot roll-over shape as well as storage and release of energy from the prosthesis at the appropriate times. The device can also allow for automatic adaptation for different heel heights, allowing a user to use a variety of different shoes. The devices can also be used in walking machines, legged robots, and toys.

The prosthetic or orthotic foot can be manufactured from a variety of compositions and a variety of combination of compositions. The prosthetic foot can comprise a composition selected from the group consisting of stainless steel, copper, aluminum, titanium, metal matrix composite, metal alloy, such as NITINOL, DELRIN (acetal), acrylonitrile butadiene styrene (ABS), nylon, polypropylene, polybromate, polycarbonate, glycolised polyethylene terephthalate (PETg) copolyester, polytetrafluorethylene (PTFE), ePTFE, polypropylene, or another polymer, glass fiber-resin composites, other composite materials, and the like, and, optionally, that can be easily machined, compression molded, or injection molded to the required shape.

The prosthetic foot can be shaped and sized for purposes of mass manufacture in a standard size and shape. In the alternative, it can be manufactured to specifications for a single individual. The prosthetic foot can be manufactured using modular components, the modular components having different shapes, sizes, and compositions.

The ankle of the prosthetic foot can comprise a locking mechanism, for example the locking mechanism can be selected from the group consisting of, a pair of cams, a ratchet mechanism, a ball joint (such as disclosed in U.S. Pat. No. 6,217,249 to Merlo, issued Apr. 17, 2001), selectively engageable and disengagable mechanisms, and joint locking mechanisms as disclosed in, for example, U.S. Pat. No. 6,159,248 to Gramnas, issued Dec. 12, 2000, U.S. Pat. No. 6,436,149 to Rincoe, issued Aug. 20, 2002). The prosthetic system can also be combined with at least one microprocessor comprising a software program or other instructional means that in combination can provide a control means. The control means can measure the torsion within the system and/or the angular movement of the ankle and thereby control the engagement means and the torsion means during each step cycle or gait cycle. Such microproccessors and software programs are well known to those of skill in the art.

Table 1 discloses the various elements used to create the second design iteration, an exemplary embodiment of the invention

TABLE 1

| Structural Group | Part Name | Function | Equivalent Reference No. |
|---|---|---|---|
| Shank | Pylon | Provides load-based deflection to actuate clutch | 4, 17 |
| Shank | Housing | Supports pylon, transfers moments to housing arbor | 18 |
| Shank | Housing Arbor | Shank side of wrap spring clutch | 19 |
| Intermediate | Torque Arbor | Intermediate side of wrap spring clutch | 20 |
| Intermediate | Torque Transfer Cap | Transfers moments from clutch to stiff bumper(s) | 21 |
| Foot | Housing Base, Bars | Supports shaft and sandwiches footplate | 23 |
| Foot | Housing Base, Socket | Holds stiff bumper(s), supports shaft, clamps footplate | 23 |
| Foot | Shaft (+/− bushings) | Supports shank and intermediate parts | 22 |
| Foot | Footplate | Provides contact with surface | 3, 13 |
| Intermediate | Clutch Spring | Transfers moments between arbors | 24 |
| Intermediate | Clutch Collar | Rotates to engage or disengage clutch spring | 30 |
| Intermediate | Neutralizing Bumper | Low stiffness bumper(s) inside arbors that neutralize foot when clutch is disengaged | 11 |
| Intermediate | Neutralizing Block | Secured inside arbors to compress neutralizing bumper(s) | 25 |
| Intermediate | High Stiffness Bumper | Provides high stiffness | 12 |
| Intermediate | Engagement Linkage | Transfers displacements from pylon to clutch collar | 26 |

There now follows a non-exhaustive list of different devices and/or mechanisms known to those of skill in the art that can be used with the invention.

Engagement Means

Types of Clutch

Automatic clutch, backstopping clutch, ball clutch, bidirectional clutch, brake-clutch combination, cam clutch, cam and roller clutch, centrifugal clutch, cone clutch, detent slip clutch, disc clutch, dog clutch, double clutch, double-spring clutch, dual-spring slip clutch, duplex clutch, driving clutch, eddy current clutch, electrostatic clutch, expanding shoe clutch, externally controlled positive clutch, external control clutch, internal control clutch, fixed-field clutch, fluid clutch, free-wheeling clutch, friction clutch, multiple disc clutch, détente clutch, plate clutch, hysteresis clutch, indexing clutch, internally controlled clutch, jaw clutch, lawnmower clutch, bidirectional locking clutch, locking clutch, magnetic friction clutch, magnetic particle clutch, magnetic fluid clutch, magnetostrictive clutch, mechanical clutch, mercury-gland clutch, multidisk clutch, multistation clutch, one-way clutch, overload relief clutch, overriding clutch, overrunning clutch, planetary transmission clutch, plate clutch, roller clutch, roller clutch, rotating-field clutch, sliding-key clutch, slip clutch, spiral-band clutch, sprag clutch, spring clutch, spring and ball radial detent clutch, station clutch, tooth clutch, torque limiting clutch, trip clutch, wedging ball or roller clutch, and wrap spring clutch.

Wrap Spring Clutch

The wrap spring clutch (FIG. 14, 14) is a mechanism having a spring coil (24) wrapped around a pair of equal diameter cylindrical arbors (19 and 20). As the clutch was used as to engage the stiffness interface, one of the arbors (19) comprised a part of the shank structure (15) while the other arbor (20) comprised part of the intermediate structure (16). Thus when the clutch was engaged, forces applied by the shank structure (15) would be transmitted through the clutch spring to the intermediate structure (16), effectively locking them together and forcing all deflection to occur at the high stiffness interface between the intermediate structure (16) and the foot structure (3).

Types of Brake

Air brakes, anti-lock brakes, coaster brakes, disc brakes, drum brakes, eddy current brakes, electric brakes, friction brakes, hub brakes, hydraulic brakes, multi-disc brakes, power brakes, rim brakes, spoon brakes, band brakes, and caliper brakes.

Types of Lock

Cruciform lock, cylinder lock, deadbolt lock, disc tumbler lock, electronic lock, magnetic lock, electric strike lock, level tumbler lock, Chubb detector lock, protector lock, padlock, pin tumbler lock, wafer tumbler lock, warded lock, five lever lock, keycard lock, rim lock, combination lock, and pin lock.

Stiffness or Torsion Means

Types of Spring

Coil or helical spring, tension spring, compression spring, leaf spring, v-spring, spiral spring, clock spring, cantilever spring, Belleville washer spring, spring washer, torsion spring, gas spring, rubber band, elastic elements, bumpers, umbrella springs, conical springs, taper springs, disc spring, and extension spring.

Types of Damper

Backdraft damper, barometric damper, butterfly damper, curtain damper, dual tube damper, flap damper, free-piston monotube damper, guillotine damper, louvre damper, sliding damper, and vibration damper.

Additional Embodiments

The size and weight of the prototype may be reduced to ensure the device is not burdensome to users and thus potentially offset the benefits of surface adaptation. The ankle moment-angle curves for one subject showed a consistent plateau region where the ankle angle was changing without a corresponding change in ankle moment, suggesting that for that subject the clutch may have been slipping. Further development of the engagement mechanism and the clutch may ensure consistent engagement and sufficient resistance to ankle moments.

The action of the adaptable ankle's high stiffness bumper may be produced by a deflecting foot plate. Such a high-deflection foot plate may be capable of consistently supporting dorsiflexion deflections of 25 degrees based on previous studies (see, for example, Leroux, A., Fung, J., and Barbeau, H., 2002, "Postural Adaptations to Walking on Inclined Surfaces: I. Normal Strategies," Gait & Pos., 15(1), pp. 67-74; Prentice, S., Hasler, E., Groves, J., and Frank, J., 2004, "Locomotor Adaptations for Changes in the Slope of the Walking Surface," Gait & Pos., 20(3), pp. 255-265; Hansen, A., Childress, D., Miff, S., Gard, S., and Mesplay, K., 2004, "The Human Ankle During Walking: Implications for Design of Biomimetic Ankle Prostheses," J. Biomech., 37(10), pp. 1467-1474; and Lay, A., Hass, C., and Gregor, R., 2006, "The Effects of Sloped Surfaces on Locomotion: A Kinematic and Kinetic Analysis," J. Biomech., 39(9), pp. 1621-1628). Development of a foot plate capable of providing such deflections under normal load levels may permit the elimination of the high stiffness bumper and allow the intermediate and foot structures to be combined into one single structure. These changes may reduce the mass and size of the adaptable ankle.

REFERENCE NUMERALS

1. Self-adapting prosthetic system
2. Ankle-foot prosthesis
3. Foot
4. Leg attachment (pylori)
5. First torsion means
6. Second torsion means
7. Engagement means
8. Optional Linkage means
9. Ankle pivot
10. Adaptable ankle
11. Low stiffness element (or bumper)
12. High stiffness element (or bumper)
13. Footplate
14. Clutch
15. Shank structure
16. Intermediate structure
17. Pylori
18. Housing
19. Housing arbor
20. Torque arbor
21. Torque transfer cap
22. Shaft
23. Housing base
24. Spring coil
25. Block
26. Engagement linkage
27. Control tang
28. Locking tang
29. Lever
30. Control or clutch collar
31. Surface The invention will be more readily understood by reference to the following examples, which are included merely for purposes of illustration of certain aspects and embodiments of the present invention and not as limitations.

EXAMPLES

Example I

Wrap Spring Clutch

The wrap spring clutch (FIG. 14, 14) comprised a spring coil (24) wrapped around a pair of equal diameter cylindrical arbors (19 and 20). The clutch used to lock out the low stiffness bumper in dorsiflexion needed to be small and light enough to fit within the reasonable dimensions of an anatomical ankle and foot, while still being capable of withstanding specific ankle moments of approximately $1.7 \text{Nm} \cdot \text{kg}^{-1}$ (based on data from Hansen et al., 2004, "The Human Ankle During Walking: Implications for Design of Biomimetic Ankle Prostheses," J. Biomech., 37(10): 1467-1474). For a 100 kg person, this would result in an ankle moment of 1700 Nm. During steady state walking, the clutch would be required to resist an external dorsiflexion moment only, thus a unidirectional clutch, such as the wrap spring clutch, would be acceptable, although other clutch systems may be considered.

Wrap spring clutch mechanisms have been used in other rehabilitation applications due to the relatively large moment resistance such a mechanism can provide relative to the size and weight of the clutch system. The application of wrap spring clutches to prosthetics and orthotics has thus far been primarily in upper limb prosthetic components and orthotic knee joints (Kangude et al., 2009, "Single Channel Hybrid FES Gait System Using an Energy Storing Orthosis: Preliminary Design," Proc. IEEE Eng. Med. Bio. Soc., 2009: 6798-6801; Irby et al., 1999, "Optimization and Application of a Wrap-Spring Clutch to a Dynamic Knee-Ankle-Foot Orthosis," IEEE Trans. Rehabil. Eng., 7(2): 130-134).

The clutch spring used in this example was the drive spring of a Warner Electric CB-7 clutch-brake system, rated for 1700 Nm (Warner Electric, South Beloit, Ill., USA). Due to the size and mass of the commercial clutch system, only the spring (24) was used for this application. The clutch arbors (19 and 20) were custom fabricated from 2024 high strength aluminum alloy.

Example II

Adaptable Ankle

The adaptable ankle model presented in FIGS. 10C and D comprised three structures, shown assembled separately in FIG. 12 with non-structural parts removed. The shank structure (FIG. 12A and white structures in FIG. 10) interfaced the adaptable ankle with the subject's socket and transferred moments to the driving arbor of the wrap spring clutch. The intermediate structure (FIG. 12B and gray structures in FIG. 10) received moments from the driven arbor of the wrap spring clutch, formed a track within which the left side of the shank structure rested, and applied forces to the high stiffness bumper. The foot structure (FIG. 12C and black structures in FIG. 10) supported the shaft about which all structures rotated, supported the high stiffness bumper, and held the footplate.

Between the intermediate structure and the foot structure rested the high stiffness bumper (FIG. 13). It was made from nominally 90 Shore A durometer polyurethane rubber (samples measured at approximately 110 Shore A). The rubber bumper rested in a socket in one side of the base structure (shown removed in FIG. 12) with the top of the bumper resting against one part of the intermediate structure while the bottom of the bumper rested against a rib that protruded from the base structure wall (visible in FIG. 12C). This bumper was compressed until the ankle achieved a dorsiflexion angle of approximately 15 degrees, at which time the shank structure physically rested against the socket side of the foot structure (bottomed out).

Between the shank structure and the intermediate structure rested the low stiffness bumpers. These bumpers were intended to neutralize the orientation of the footplate during swing, when the prosthesis was unloaded. To achieve this neutralization, the bumpers were cast as modular sections from Oomoo 30, a silicone rubber from Smooth-On with a nominal durometer of 30 Shore A at full cure. These bumpers were assembled in the interior space of the wrap spring clutch arbors. Each arbor had a block bolted inside. The bumpers filled the space between these "neutralizing" blocks such that when one arbor rotated with respect to the other, one of the bumpers was being compressed (FIG. 15. 7). This arrangement provided neutralization during swing and low stiffness in both plantarflexion and dorsiflexion during early stance when the prototype "finds" the surface.

The operation of the adaptable ankle required that the clutch be engaged and disengaged at different phases of the gait cycle. Upon being loaded by the user, the clutch must be engaged to resist externally applied dorsiflexion moments, whereas upon being unloaded the clutch must be disengaged to permit neutralization. Therefore a commercially available shock absorbing pylori (Endolite Telescopic-Torsion Pylori) was used to provide a load-based deflection that could be utilized to engage the clutch (FIG. 8). The displacement at the shock absorbing pylori was amplified by a linkage with an approximate gain of two.

When the adaptable ankle was unloaded, the shock absorbing pylori would be at full extension. In full extension, the end of the wrap spring was being lifted away from the arbors, resulting in disengagement. As the pylori received load, the shock absorbing pylori compressed and the descending link (FIG. 8) moved downward, permitting the lever to rotate downward, releasing tension on the string. The string (8) was affixed to the control collar (30). The resting interior diameter of the clutch spring was smaller than the outer diameter of the arbors, thus when under no external influence, the clutch spring would rest against the arbors. When the control collar (30) was rotated by the lever pulling up on the string (8), the end of the clutch spring was rotated in a direction that would cause an increase in the interior diameter of the clutch spring, preventing the coil from gripping the arbors and therefore disengaging the clutch. Thus the clutch was disengaged during swing, permitting neutralization.

Example III

Testing

The adaptable ankle prototype was tested mechanically as well as on human subjects. The mechanical fatigue testing was performed based on the ISO 10328 cyclic test standards for prosthetic foot and ankle systems.

The cyclic fatigue testing was performed using a custom-built apparatus that applied separate heel and forefoot loads produced by pneumatic pistons. The adaptable ankle was tested to 100,000 cycles at the P4 load level, based on gait parameters for persons with body masses of 60-80 kg or 130-175 lb. The procedure was modified to account for the adaptable ankle prototype's unique function.

Results from the mechanical testing indicated that the central coil of the clutch spring, the coil which transitions from one arbor to the other, was causing damage that eroded material from the arbor rims to a depth of 0.51 mm). No other significant wear was observed. The clutch continued to hold proof test forces after cyclic testing.

The human subject testing was performed at the VA Chicago Motion Analysis Research Laboratory, where a gait analysis was performed on three subjects, each using both the adaptable ankle and their normal prosthesis to walk on level and sloped surfaces for the purpose of determining whether the prototype was adapting to sloped surfaces. Human subject testing was performed as previously described by Williams et al. and Hansen et al. (Williams et al. 2009 supra; Hansen et al. 2004 supra). The ramp spanned two force platforms, thus ankle moment data were only available during single limb support (high stiffness region of the plot in FIG. 5). However, the amount of translation of the high stiffness portion of the ankle moment vs angle curve along the ankle angle axis is indicative of the location of the equilibrium point for a given condition. The study was approved by the Northwestern University Institutional Review Board. All three participants provided informed consent.

Each individual subject and the group as a whole (FIG. 9) demonstrated greater apparent slope adaptation when using the adaptable ankle prototype as compared to their normal prostheses. One subject tested in the present study had participated in the testing of the proof-of-concept device, while the other two had not.

Example IV

Use of Potentiometers or Encoders to Control Locking-Unlocking Mechanisms

Potentiometers or encoders can measure these angles during use of the device. In early stance, the locking mechanism may be unlocked. When the rotational sensor indicated that a minimum dorsiflexion angle is reached (at time 1), the system will signal to engage the locking mechanism. This mechanism remains engaged until this angle is approached at the end of stance phase (at time 2), at which time the system unlocks and allows the neutralizing springs to bring the ankle back to neutral for swing phase.

Example V

Use of Forefoot Pressure Sensors to Control Locking-Unlocking Mechanisms

An alternative way to control the locking and unlocking mechanism is to use a forefoot pressure sensor. In early stance, the ankle plantarflexes until the forefoot contacts the walking surface. At this first contact with the forefoot pressure sensor, the locking mechanism may be engaged. Forefoot contact remains until the toe comes off of the ground at the end of stance. At this time, the pressure goes to zero and the locking mechanism could be unlocked, allowing the neutralizing springs to bring the ankle back to neutral for swing phase.

Those skilled in the art will appreciate that various adaptations and modifications of the just-described embodiments can be configured without departing from the scope and spirit of the invention. Other suitable techniques and methods known in the art can be applied in numerous specific modalities by one skilled in the art and in light of the description of the present invention described herein. Therefore, it is to be understood that the invention can be practiced other than as specifically described herein. The above description is intended to be illustrative, and not restrictive. Many other embodiments will be apparent to those of skill in the art upon reviewing the above description. The scope of the invention should, therefore, be determined with reference to the appended claims, along with the full scope of equivalents to which such claims are entitled.

We claim:

1. A passive, self-adapting ankle-foot prosthetic system comprising a shank structure, a foot structure, an intermediate element interposed between the shank structure and the foot structure, and a clutch;
   the foot structure comprising a foot plate, a shaft for rotatably connecting the foot structure to the intermediate element, and a housing including a base configured to receive the shaft;
   the intermediate structure comprising a first arbor;
   the shank structure comprising second arbor and a shock-absorbing pylon for engaging the clutch upon loading the prosthetic system to resist externally-applied dorsiflexion moments and disengaging the clutch upon unloading the prosthetic system to return the foot structure to a neutral orientation relative to the shank structure;
   the clutch comprising a spring being operatively interposed between the first arbor and second arbor on the shaft and a collar for selectively engaging the spring;
   an engagement linkage operatively connecting the pylon to the collar;
   a first bumper received in the housing base and interposed between the intermediate element and the foot structure such that the first bumper is compressed during dorsiflexion; and
   one or more second bumpers interposed between the shank structure and the intermediate element for returning an unloaded foot structure to the neutral orientation;
   the first bumper and the one or more second bumpers being in series.

2. The system of claim 1 wherein the engagement linkage further comprises a lever and means for attaching the lever to the spring selected from the group consisting of a string, a wire, a cable, a rod, a thread, a tape, a chain, a ribbon, a cord, a fiber, a line and a filament.

3. The system of claim 1 wherein the stiffness of the first bumper is approximately three times greater that the stiffness of the one or more second bumpers.

4. A passive, self-adapting ankle-foot orthotic system comprising a shank structure, a foot structure, an intermediate element interposed between the shank structure and the foot structure, and a clutch;
   the foot structure comprising a foot plate, a shaft for rotatably connecting the foot structure to the intermediate element, and a housing including a base configured to receive the shaft;
   the intermediate structure comprising a first arbor;
   the shank structure comprising second arbor and a shock-absorbing pylon for engaging the clutch upon loading the prosthetic system to resist externally-applied dorsiflexion moments and disengaging the clutch upon unloading the prosthetic system to return the foot structure to a neutral orientation relative to the shank structure;
   the clutch comprising a spring being operatively interposed between the first arbor and second arbor on the shaft and a collar for selectively engaging the spring;
   an engagement linkage operatively connecting the pylon to the collar;
   a first bumper received in the housing base and interposed between the intermediate element and the foot structure such that the first bumper is compressed during dorsiflexion; and
   one or more second bumpers interposed between the shank structure and the intermediate element for returning an unloaded foot structure to the neutral orientation;
   the first bumper and the one or more second bumpers being in series.

5. The system of claim 4 wherein the engagement linkage further comprises a lever and means for attaching the lever to the spring selected from the group consisting of a string, a wire, a cable, a rod, a thread, a tape, a chain, a ribbon, a cord, a fiber, a line and a filament.

6. The system of claim 4 wherein the stiffness of the first bumper is approximately three times greater that the stiffness of the one or more second bumpers.

* * * * *